US 11,684,750 B2

(12) United States Patent
Piferi

(10) Patent No.: US 11,684,750 B2
(45) Date of Patent: Jun. 27, 2023

(54) EXTENSION TUBE ASSEMBLY AND RELATED MEDICAL FLUID TRANSFER SYSTEMS AND METHODS

(71) Applicant: ClearPoint Neuro, Inc., Irvine, CA (US)

(72) Inventor: Peter G. Piferi, Orange, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 400 days.

(21) Appl. No.: 16/887,161

(22) Filed: May 29, 2020

(65) Prior Publication Data

US 2021/0100977 A1    Apr. 8, 2021

Related U.S. Application Data

(60) Provisional application No. 62/937,911, filed on Nov. 20, 2019, provisional application No. 62/912,324, filed on Oct. 8, 2019.

(51) Int. Cl.
*A61M 25/00* (2006.01)
*A61M 39/10* (2006.01)
*A61B 90/11* (2016.01)

(52) U.S. Cl.
CPC ......... *A61M 25/0097* (2013.01); *A61B 90/11* (2016.02); *A61M 25/0023* (2013.01);
(Continued)

(58) Field of Classification Search
CPC .......... A61M 25/0097; A61M 25/0023; A61M 25/0084; A61M 25/0089; A61M 39/10;
(Continued)

(56) References Cited

U.S. PATENT DOCUMENTS 3,352,306 A   11/1967  Hrisch
3,540,447 A   11/1970  Howe
(Continued)

FOREIGN PATENT DOCUMENTS

CA    2655515 A1   8/2010
EP    1029509 A1   8/2000
(Continued)

OTHER PUBLICATIONS

Bankiewicz et al. "Convection-Enhanced Delivery of AAV Vector in Parkinsonian Monkeys; In Vivo Detection of Gene Expression and Restoration of Dopaminergic Function Using Pro-drug Approach" Experimental Neurology 164:2-14 (2000).
(Continued)

*Primary Examiner* — James D Ponton
*Assistant Examiner* — Neeraja Gollamudi
(74) *Attorney, Agent, or Firm* — Myers Bigel, P.A.

(57) ABSTRACT

Devices for transferring fluid to or from a subject include an extension tube assembly with an axially extending inner tube configured to couple to an elongate tubular cannula having opposing proximal and distal ends with an axially extending lumen and an axially extending inner tube. The inner tube extending through the tubular cannula defines an exposed needle tip and is in fluid communication with the inner tube of the extension tube assembly. The needle tip extends out of a distal end of the tubular cannula a suitable distance.

14 Claims, 11 Drawing Sheets

(52) U.S. Cl.
CPC ........ *A61M 25/0084* (2013.01); *A61M 39/10*
(2013.01); *A61M 2025/0089* (2013.01); *A61M*
*2039/1077* (2013.01)

(58) Field of Classification Search
CPC .. A61M 2039/1077; A61M 2025/0004; A61M
2025/0006; A61M 2025/0042; A61M
25/0043
See application file for complete search history.

(56) References Cited

U.S. PATENT DOCUMENTS

| | | |
|---|---|---|
| 3,824,157 A | 7/1974 | Macur |
| 3,856,009 A | 12/1974 | Winnie |
| 4,149,535 A | 4/1979 | Volder |
| 4,239,042 A | 12/1980 | Asai |
| 4,265,928 A | 5/1981 | Braun |
| 4,327,722 A | 5/1982 | Groshong et al. |
| 4,449,532 A | 5/1984 | Storz |
| 4,531,943 A | 7/1985 | Van Tassel et al. |
| 4,543,091 A | 9/1985 | Froning et al. |
| 4,543,092 A | 9/1985 | Mehler et al. |
| 4,597,421 A | 7/1986 | Wells |
| 4,623,789 A | 11/1986 | Ikeda et al. |
| 4,629,450 A | 12/1986 | Suzuki et al. |
| 4,705,511 A | 11/1987 | Kocak |
| 4,738,658 A | 4/1988 | Magro et al. |
| 4,739,768 A | 4/1988 | Engelson |
| 4,781,691 A | 11/1988 | Gross |
| 4,820,349 A | 4/1989 | Saab |
| 4,846,799 A | 7/1989 | Tanaka et al. |
| 4,897,077 A | 1/1990 | Cicciu et al. |
| 4,955,863 A | 9/1990 | Walker et al. |
| 4,978,334 A | 12/1990 | Toye et al. |
| 4,995,866 A | 2/1991 | Amplatz et al. |
| 5,069,673 A | 12/1991 | Shwab |
| 5,380,292 A | 1/1995 | Wilson |
| 5,562,626 A | 10/1996 | Sanpietro |
| 5,699,801 A | 12/1997 | Atalar et al. |
| 5,720,720 A | 2/1998 | Laske et al. |
| 5,722,985 A | 3/1998 | Pettus |
| 5,792,144 A | 8/1998 | Fischell et al. |
| 5,833,662 A | 11/1998 | Stevens |
| 5,851,203 A | 12/1998 | Van Muiden |
| 5,857,999 A | 1/1999 | Quick et al. |
| 5,871,470 A | 2/1999 | McWha |
| 5,902,282 A | 5/1999 | Balbierz |
| 5,919,171 A | 7/1999 | Kira et al. |
| 5,928,145 A | 7/1999 | Ocali et al. |
| 5,935,122 A | 8/1999 | Fourkas et al. |
| 6,020,196 A | 2/2000 | Hu et al. |
| 6,026,316 A | 2/2000 | Kucharczyk et al. |
| 6,030,369 A | 2/2000 | Engelson et al. |
| 6,042,579 A | 3/2000 | Elsberry et al. |
| 6,050,992 A | 4/2000 | Nichols |
| 6,093,180 A | 7/2000 | Elsberry |
| 6,167,311 A | 12/2000 | Rezai |
| 6,186,986 B1 | 2/2001 | Berg et al. |
| 6,231,591 B1 | 5/2001 | Desai |
| 6,263,229 B1 | 7/2001 | Atalar et al. |
| 6,284,971 B1 | 9/2001 | Atalar et al. |
| RE37,410 E | 10/2001 | Brem et al. |
| 6,309,634 B1 | 10/2001 | Bankiewicz et al. |
| 6,336,915 B1 | 1/2002 | Scarfone et al. |
| 6,356,786 B1 | 3/2002 | Rezai et al. |
| 6,405,079 B1 | 6/2002 | Ansarinia |
| 6,438,423 B1 | 8/2002 | Rezai et al. |
| 6,461,296 B1 | 10/2002 | Desai |
| 6,524,299 B1 | 2/2003 | Tran et al. |
| 6,526,318 B1 | 2/2003 | Ansarinia |
| 6,533,751 B2 | 3/2003 | Cragg et al. |
| 6,539,263 B1 | 3/2003 | Schiff et al. |
| 6,551,290 B1 | 4/2003 | Elsberry et al. |
| 6,585,694 B1 | 7/2003 | Smith et al. |
| 6,606,513 B2 | 8/2003 | Lardo et al. |
| 6,609,030 B1 | 8/2003 | Rezai et al. |
| 6,628,980 B2 | 9/2003 | Atalar et al. |
| 6,641,555 B1 | 11/2003 | Botich et al. |
| 6,641,564 B1 | 11/2003 | Kraus |
| 6,675,033 B1 | 1/2004 | Lardo et al. |
| 6,689,142 B1 | 2/2004 | Tremaglio et al. |
| 6,701,176 B1 | 3/2004 | Halperin et al. |
| 6,708,064 B2 | 3/2004 | Rezai |
| 6,904,307 B2 | 6/2005 | Karmarkar et al. |
| 7,037,295 B2 | 5/2006 | Tiernan et al. |
| 7,182,944 B2 | 2/2007 | Bankiewicz |
| 7,329,262 B2 | 2/2008 | Gill |
| 7,341,577 B2 | 3/2008 | Gill |
| 7,351,239 B2 | 4/2008 | Gill |
| 7,371,225 B2 | 5/2008 | Oldfield et al. |
| 7,780,692 B2 | 8/2010 | Nance et al. |
| 7,815,623 B2 | 10/2010 | Bankiewicz et al. |
| 7,892,203 B2 | 2/2011 | Lenker et al. |
| 7,951,110 B2 | 5/2011 | Bishop et al. |
| 8,128,600 B2 | 3/2012 | Gill |
| 8,175,677 B2 | 5/2012 | Sayler et al. |
| 8,195,272 B2 | 6/2012 | Piferi et al. |
| 8,315,689 B2 | 11/2012 | Jenkins et al. |
| 8,340,743 B2 | 12/2012 | Jenkins et al. |
| 8,348,892 B2 | 1/2013 | Lenker et al. |
| 8,374,677 B2 | 2/2013 | Piferi et al. |
| 8,597,277 B2 | 12/2013 | Lenker et al. |
| 8,827,987 B2 | 9/2014 | Fielder et al. |
| 8,900,214 B2 | 12/2014 | Nance et al. |
| 9,044,577 B2 | 6/2015 | Bishop et al. |
| 9,050,419 B2 | 6/2015 | Farnan |
| 9,452,241 B2 | 9/2016 | Gill et al. |
| 9,498,575 B2 | 11/2016 | Flores |
| 9,572,928 B2 | 2/2017 | Shifflette et al. |
| 9,610,048 B2 | 4/2017 | Vij et al. |
| 9,891,296 B2 | 2/2018 | Piferi |
| 10,105,485 B2 | 10/2018 | Piferi et al. |
| 10,576,247 B2 | 3/2020 | Flores et al. |
| 11,022,664 B2 | 6/2021 | Piferi |
| 2002/0052576 A1* | 5/2002 | Massengale ...... A61M 25/0074 604/164.01 |
| 2002/0087152 A1 | 7/2002 | Mikus et al. |
| 2002/0091372 A1 | 7/2002 | Cragg et al. |
| 2002/0095081 A1 | 7/2002 | Vilsmeier |
| 2002/0114780 A1 | 8/2002 | Bankiewicz et al. |
| 2002/0141980 A1 | 10/2002 | Bankiewicz et al. |
| 2002/0183763 A1 | 12/2002 | Callol et al. |
| 2003/0028095 A1 | 2/2003 | Tulley et al. |
| 2003/0050557 A1 | 3/2003 | Susil et al. |
| 2003/0073934 A1 | 4/2003 | Putz |
| 2003/0130575 A1 | 7/2003 | Desai |
| 2003/0216714 A1 | 11/2003 | Gill |
| 2004/0044329 A1 | 3/2004 | Trudell |
| 2004/0046557 A1 | 3/2004 | Karmarkar et al. |
| 2004/0064098 A1 | 4/2004 | Cuschieri et al. |
| 2004/0068190 A1 | 4/2004 | Cespedes |
| 2004/0092879 A1 | 5/2004 | Kraus et al. |
| 2004/0199129 A1 | 10/2004 | DiMatteo |
| 2004/0209810 A1 | 10/2004 | Gill et al. |
| 2004/0215162 A1 | 10/2004 | Putz |
| 2004/0249261 A1* | 12/2004 | Torchia ............ A61B 18/22 606/15 |
| 2005/0004504 A1 | 1/2005 | Frye et al. |
| 2005/0112065 A1 | 5/2005 | Drummond et al. |
| 2005/0148865 A1 | 7/2005 | Weber |
| 2005/0154297 A1 | 7/2005 | Gill |
| 2005/0256503 A1 | 11/2005 | Hall |
| 2006/0052750 A1 | 3/2006 | Lenker et al. |
| 2006/0073101 A1 | 4/2006 | Oldfield et al. |
| 2006/0129126 A1 | 6/2006 | Kaplitt et al. |
| 2006/0135945 A1 | 6/2006 | Bankiewicz et al. |
| 2006/0217664 A1 | 9/2006 | Hattler et al. |
| 2007/0088295 A1 | 4/2007 | Bankiewicz |
| 2007/0110798 A1 | 5/2007 | Drummond et al. |
| 2007/0167736 A1 | 7/2007 | Dietz et al. |
| 2007/0179455 A1 | 8/2007 | Geliebter et al. |
| 2007/0250021 A1 | 10/2007 | Brimhall et al. |
| 2007/0254842 A1 | 11/2007 | Bankiewicz |
| 2008/0103456 A1 | 5/2008 | Johnson et al. |

(56) References Cited

U.S. PATENT DOCUMENTS

| | | | |
|---|---|---|---|
| 2008/0119821 A1 | 5/2008 | Agnihotri et al. |
| 2008/0215008 A1 | 9/2008 | Nance et al. |
| 2008/0228168 A1 | 9/2008 | Mittermeyer et al. |
| 2008/0319377 A1 | 12/2008 | Keenan |
| 2009/0088695 A1 | 4/2009 | Kapur et al. |
| 2009/0088730 A1 | 4/2009 | Hoofnagle et al. |
| 2009/0112084 A1 | 4/2009 | Piferi et al. |
| 2009/0118610 A1 | 5/2009 | Karmarkar et al. |
| 2009/0143764 A1 | 6/2009 | Nelson |
| 2009/0171184 A1 | 7/2009 | Jenkins et al. |
| 2009/0198218 A1 | 8/2009 | Gill et al. |
| 2009/0209937 A1 | 8/2009 | Rogawski et al. |
| 2009/0281453 A1 | 11/2009 | Tsonton et al. |
| 2010/0130958 A1 | 5/2010 | Kang et al. |
| 2010/0198052 A1 | 8/2010 | Jenkins et al. |
| 2010/0217228 A1 | 8/2010 | Grahn et al. |
| 2010/0217236 A1 | 8/2010 | Gill et al. |
| 2010/0228122 A1 | 9/2010 | Keenan et al. |
| 2010/0317961 A1 | 12/2010 | Jenkins et al. |
| 2010/0318061 A1 | 12/2010 | Derrick et al. |
| 2010/0318064 A1 | 12/2010 | Derrick et al. |
| 2011/0282319 A1 | 11/2011 | Gill |
| 2012/0123391 A1 | 5/2012 | Gill et al. |
| 2012/0310182 A1 | 12/2012 | Fielder et al. |
| 2013/0006095 A1 | 1/2013 | Jenkins et al. |
| 2013/0030408 A1 | 1/2013 | Piferi et al. |
| 2013/0150712 A1 | 6/2013 | Field |
| 2013/0226094 A1 | 8/2013 | Ahmed et al. |
| 2014/0257168 A1 | 9/2014 | Gill |
| 2014/0343500 A1 | 11/2014 | Fielder et al. |
| 2015/0080708 A1 | 3/2015 | Piferi |
| 2015/0374908 A1 | 12/2015 | Piferi |
| 2016/0074626 A1 | 3/2016 | Weadock et al. |
| 2016/0100895 A1 | 4/2016 | Piferi et al. |
| 2016/0213312 A1* | 7/2016 | Singh | A61B 5/6848 |
| 2016/0346505 A1 | 12/2016 | Gill et al. |
| 2017/0197017 A1 | 7/2017 | Martin |
| 2017/0232229 A1* | 8/2017 | Flores | A61M 25/0097 |
| | | | 604/506 |
| 2018/0303560 A1 | 10/2018 | Pandey et al. |
| 2019/0255282 A1 | 8/2019 | Inukai et al. |
| 2019/0346516 A1 | 11/2019 | Piferi |

FOREIGN PATENT DOCUMENTS

| | | | |
|---|---|---|---|
| EP | 1482851 A1 | 12/2004 |
| EP | 1491154 A1 | 12/2004 |
| EP | 1334740 A1 | 8/2009 |
| GB | 1255551 A | 12/1971 |
| JP | 2002509767 A | 4/2002 |
| JP | 2004147830 A | 5/2004 |
| WO | 9904849 A1 | 2/1999 |
| WO | 9949909 A2 | 10/1999 |
| WO | 02053205 A2 | 7/2002 |
| WO | 03077785 A1 | 9/2003 |
| WO | 2004031348 A2 | 4/2004 |
| WO | 2008020237 A2 | 2/2008 |
| WO | 2008020241 A2 | 2/2008 |
| WO | 2008144585 A1 | 11/2008 |
| WO | 2008144775 A1 | 11/2008 |
| WO | 2009042135 A2 | 4/2009 |
| WO | 2009047490 A2 | 4/2009 |
| WO | 2009066130 A1 | 5/2009 |
| WO | 2009101397 A1 | 8/2009 |
| WO | 2010040970 A2 | 4/2010 |
| WO | 2011098768 A1 | 8/2011 |
| WO | 2011098769 A1 | 8/2011 |
| WO | 2012178169 A2 | 12/2012 |
| WO | 2013050148 A1 | 4/2013 |
| WO | 2014089373 A1 | 6/2014 |
| WO | 2019030761 A1 | 2/2019 |

OTHER PUBLICATIONS

Chen et al. "Variables affecting convection-enhanced delivery to the striatum: a systematic examination of rate of infusion, cannula size, infusate concentration, and tissue-cannula sealing time" Journal of Neurosurgery 90:315-320 ( 1999).

Chen et al. "Combination Therapy with Irinotecan and Protein Kinase C Inhibitors in Malignant Glioma" Cancer 97(9 Suppl):2363-2373 (2003).

Chen et al. "Surface properties, more than size, limiting convective distribution of virus-sized particles and viruses in the central nervous system" Journal of Neurosurgery 103:311-319 (2005).

Cunningham et al. "Distribution of AAV-TK following intracranial convection-enhanced delivery into rats" Cell Transplantation 9(5):585-594 (2000) (Abstract Only).

Groothuis, Dennis R. "The blood-brain and blood-tumor barriers: A review of strategies for increasing drug delivery" Neuro-Oncology 2:45-59 (2000).

Hadaczek et al. "Convection-Enhanced Delivery of Adeno-Associated Virus Type 2 (AAV2) into the Striatum and Transport of AAV2 Within Monkey Brain" Human Gene Therapy 17:291-302 (2006).

Hadaczek et al. "The 'Perivascular Pump' Driven by Arterial Pulsation is a Powerful Mechanism for the Distribution of Therapeutic molecules within the Brain" Molecular Therapy 14(1):69-78 (2006).

Krauze et al. "Real-time Imaging and Quantification of Brain Delivery of Liposomes" Pharmaceutical Research 23 (11):2493-2504 (2006).

Krauze et al. "Reflux-free cannula for convection-enhanced high speed delivery of therapeutic agents" Journal of Neurosurgery 103:923-929 (2005).

Laske et al. "Chronic interstitial infusion of protein to primate brain: determination of drug distribution and clearance with single-photon emission computerized tomography imaging" Journal of Neurosurgery 87:586-594 (1997).

Lieberman et al. "Convection-enhanced distribution of large molecules in gray matter during interstitial drug infusion" Journal of Neurosurgery 82:1021-1029 (1995).

Lonser et al. "Successful and safe perfusion of the primate brainstem: in vivo magnetic resonance imaging of macromolecular distribution during infusion" Journal of Neurosurgery 97:905-913 (2002).

Mamot et al. "Extensive distribution of liposomes in rodent brains and brain tumors following convection-enhanced delivery" Journal of Neuro-Oncology 68:1-9 (2004).

Mardor et al. "Monitoring Response to Convection-enhanced Taxol Delivery in Brain Tumor Patients Using Diffusion-weighted Magnetic Resonance Imaging" Cancer Research 61:4971-4973 (2001).

Marshall et al. "Biocompatibility of Cardiovascular Gene Delivery Catheters with Adenovirus Vectors: An Important Determinant of the Efficiency of Cardiovascular Gene Transfer" Molecular Therapy 1(5):423-429 (2000).

Morrison et al. "Focal delivery during direct infusion to brain: role of flow rate, catheter diameter, and tissue mechanics" American Journal of Physiology—Regulatory, Integrative and Comparative Physiology 277:R1218-R1229 (1999).

Morrison et al. "High-flow microinfusion: tissue penetration and pharmacodynamics" American Journal of Physiology—Regulatory, Integrative and Comparative Physiology 266:R292-R305 (1994).

Naimark et al. "Adenovirus-Catheter Compatibility Increases Gene Expression After Delivery to Porcine Myocardium" Human Gene Therapy 14:161-166 (2003).

Pardridge, William M. "Drug Delivery to the Brain" Journal of Cerebral Blood Flow and Metabolism 17:713-731 (1997).

Pardridge, William M. "The Blood-Brain Barrier: Bottleneck in Brain Drug Development" NeuroRx: The Journal of the American Society for Experimental NeuroTherapeutics 2:3-14 (2005).

Patel et al. "Intraputamenal Infusion of Glial Cell Line-Derived Neurotrophic Factor in PD: A Two-Year Outcome Study" Annals of Neurology 57:298-302 (2005).

Qureshi et al. "Multicolumn Infusion of Gene Therapy Cells into Human Brain Tumors: Technical Report" Neurosurgery 46(3):663-669 (2000) (Abstract Only).

(56) References Cited

OTHER PUBLICATIONS

Richardson et al. "Interventional MRI-guided Putaminal Delivery of AAV2-GDNF for a Planned Clinical Trial in Parkinson's Disease" Molecular Therapy 19(6):1048-1057 (2011).
Rogawski, Michael A. "Convection-Enhanced Delivery in the Treatment of Epilepsy" Neurotherapeutics: The Journal of the American Society for Experimental NeuroTherapeutics 6:344-351 (2009).
Saito et al. "Convection-Enhanced Delivery of Tumor Necrosis Factor-Related Apoptosis-Inducing Ligand with Systemic Administration of Temozolomide Prolongs Survival in an Intracranial Glioblastoma Xenograft Model" Cancer Research 64:6858-6862 (2004).
Saito et al. "Distribution of Liposomes into Brain and Rat Brain Tumor Models by Convection-Enhanced Delivery Monitored with Magnetic Resonance Imaging" Cancer Research 64:2572-2579 (2004).
Tsui et al. "Stability of Adenoviral Vectors Following Catheter Delivery" Molecular Therapy 3(1):122-125 (2001).
Vogelbaum, Michael A. "Convection enhanced delivery for the treatment of malignant gliomas: symposium review" Journal of Neuro-Oncology 73:57-69 (2005).
Westphal et al. "Perspectives of cellular and molecular neurosurgery" Journal of Neuro-Oncology 70:255-269 (2004).
Hanley et al. "Safety and efficacy of minimally invasive surgery plus recombinant tissue plasminogen activator in intracerebral haemorrhage evacuation (MISTIE): a randomised, phase 2 trial" The Lancet Neurology, 15 (12):1228-1237 (2016).
Mould et al. "Minimally Invasive Surgery plus rt-PA for Intracerebral Hemorrhage Evacuation (MISTIE) Decreases Perihematomal Edema" Stroke, 44(3):627-634 (2013).

\* cited by examiner

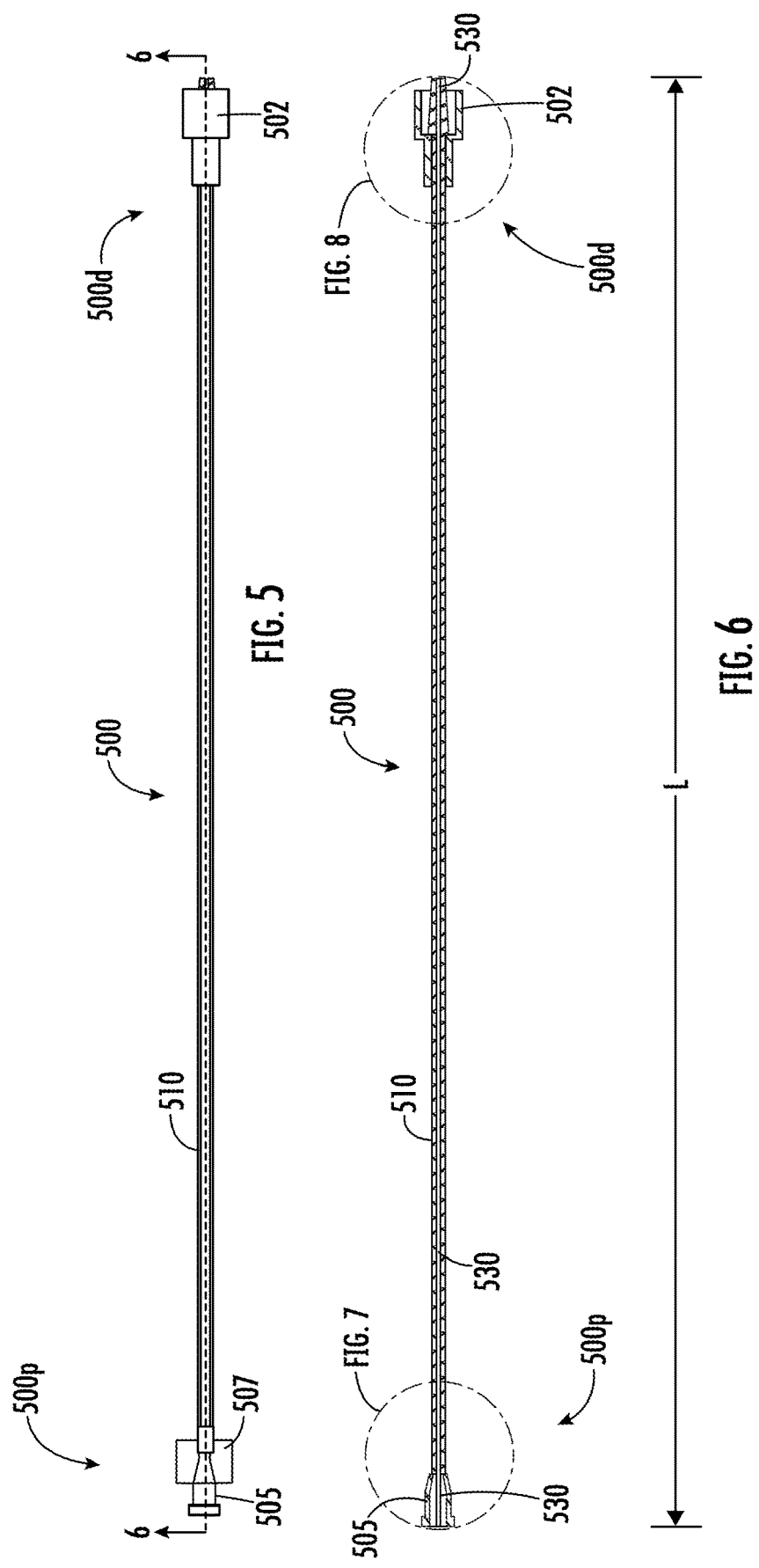

EXTENSION TUBE ASSEMBLY AND RELATED MEDICAL FLUID TRANSFER SYSTEMS AND METHODS

RELATED APPLICATIONS

This application claims the benefit of and priority to U.S. Provisional Patent Application Ser. No. 62/912,324 filed Oct. 8, 2019, and U.S. Provisional Patent Application Ser. No. 62/937,911 filed Nov. 20, 2019, the contents of which are hereby incorporated by reference as if recited in full herein.

FIELD OF THE INVENTION

The present invention relates generally to medical devices and systems and, more particularly, to devices and systems for delivering and/or withdrawing substances in vivo.

BACKGROUND

Various therapeutic and diagnostic procedures require that a substance be delivered (e.g., infused) into or aspirated from a prescribed region of a patient, such as to an intrabody target using a delivery device. It may be important or critical that the substance be delivered or removed with accuracy to the target region in the patient and without undue trauma to the patient.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention are directed to an extension tube assembly for attaching to a fluid transfer system for transferring fluid to or from a subject.

Embodiments of the invention are directed to medical extension tube assemblies for transferring fluid to or from a subject. The medical extension tube assembly includes: an outer support tube having an inner lumen and a length and opposing first and second end portions; an inner tube longitudinally extending inside the inner lumen of the outer support tube and defining a longitudinally extending open fluid flow path; a first connector coupled to the first end portion of the outer support tube; and a second connector coupled to the second end portion of the outer support tube. The inner tube has an inner diameter in a range of about 100 µm to about 750 µm. The inner tube extends out of the first end portion of the outer support sleeve into the first connector. The inner tube extends out of the second end portion of the outer support sleeve into the second connector.

The medical extension tube assembly can further include a solid filler material residing in the inner lumen of the outer support tube and surrounding the inner tube at the first and second end portions. The filler material can extend a distance into the first connection and a distance into the second connector.

The inner lumen of the outer support tube can define an open gap space surrounding the inner tube along a sub-length of the length of the outer support tube between the opposing first and second end potions.

The filler material can terminate a distance in a range of about 0.25 inches and about 1 inch from an end of the first end portion of the outer support tube. The filler material can terminate a distance in a range of about 0.25 inches and about 1 inch from an end of the second end portion of the outer support tube.

The first connector and the second connector can both be luer connectors.

The first connector can be a female luer connector and the second connector can be a male luer connector.

The inner tube can be formed of fused silica glass.

The inner tube can be formed of polyether ether ketone (PEEK).

The medical extension tube assembly can further include a coupling tube extending a distance into the inner lumen of the outer support tube at the first end portion of the outer support tube and extending a distance out of the inner lumen and into the first connector. The inner coupling tube can be closely spaced apart from and can surround the inner tube. The inner coupling tube can have a length that is in a range of about 0.1 inches and about 1 inch. The assembly can also include an adapter sleeve coupled to an outer surface of the support tube and an outer surface of the first connector.

The second connector can have an outer wall surrounding an inner channel. The inner channel can have a first segment that holds the second end portion of the outer support tube. The second connector can have a projecting member that is axially aligned with and has an end that extends forward of the outer support tube and out of the primary body of the second connector. The second connector can have an open cavity between the outer wall and the projecting member. The projecting member can have a tapered axially extending channel. The inner tube can extend through the tapered axially extending channel and can terminate at the end of the projecting member.

The medical extension tube assembly can further include filler material in the tapered axially extending channel surrounding the inner tube and in the inner lumen of the second end portion of the outer support tube surrounding the inner tube.

Other embodiments are directed to a medical intrabody fluid transfer system. The system includes an extension tube assembly coupled to a cannula assembly. The extension tube assembly has an outer support tube having an inner lumen and a length and opposing first and second end portions, an inner tube longitudinally extending inside the inner lumen of the outer support tube and defining a longitudinally extending open fluid flow path, a first connector coupled to the first end portion of the outer support tube, and a second connector coupled to the second end portion of the outer support tube. The inner tube has an inner diameter in a range of about 100 µm and about 750 µm. The inner tube extends out of the first end portion of the outer support sleeve into the first connector and the inner tube extends out of the second end portion of the outer support sleeve into the second connector. The cannula assembly includes a tubular cannula having opposing proximal and distal ends with an open axially extending lumen, an elongate inner tube extending through the lumen of the tubular cannula with a distal end defining an exposed needle tip, and flexible tubing coupled to the proximal end of the tubular cannula. The flexible tubing having an inner tube aligned with and in fluid communication with the inner tube of the tubular cannula and the inner tube of the extension tube assembly.

The inner tube of the extension tube assembly, the flexible tubing and the tubular cannula can be either PEEK or fused silica glass.

The system can further include a filter in-line with and coupled to a distal end portion of the extension tube assembly and a proximal end portion of the flexible tubing.

The flexible tubing coupled to the proximal end of the tubular cannula can have a length that is greater than a length of the outer support tube.

The first connector can be configured to directly receive a dispensing end portion of a syringe.

The tubular cannula can be rigid and be formed of a ceramic material.

The inner tube of the tubular cannula can be a first inner tube. The cannula assembly can further include a second inner tube surrounding a sub-length of the first inner tube and extending out of the tubular cannula. The distal end of the tubular cannula, and the first and second inner tubes can define a stepped configuration with a first segment having a first outer diameter that merges into a second end segment having a second smaller outer diameter having a length that extends to the exposed needle tip.

An outer surface of the tubular cannula can have a size and geometry adapted for use with a stereotactic frame with a trajectory guide having a support column sized and configured to releasably hold the tubular cannula so that the housing resides above the support column.

The inner tube of the extension assembly, the inner tube of the flexible tubing and the inner tube extending through the tubular cannula all have an inner diameter of in a range of about 100 µm and about 750 µm.

The inner tube of the extension assembly, the inner tube of the flexible tubing and the inner tube extending through the tubular cannula can all have an inner diameter that is the same, on average, over a respective length.

The inner lumen of the outer support tube can define an open gap space surrounding the inner tube along a sub-length of the length of the outer support tube between the opposing first and second end portions. The extension tube assembly can further include a solid filler material, such as epoxy, residing in the inner lumen of the outer support tube and surrounding the inner tube at (typically only) the first and second end portions of the outer support tube. The filler material can occupy a sub-length of an annular space of the inner lumen surrounding the inner tube and can extend a distance into the first connector and the second connector.

The filler material can terminate in the inner lumen of the outer support tube a distance in a range of 0.25 inches and 1 inch from an end of the first end portion of the outer support tube. The filler material can terminate in the inner lumen of the outer support tube a distance in a range of about 0.25 inches and about 1 inch from and an end of the second end portion of the outer support tube. The remaining length of the inner lumen of the outer support tube can be free of filler material providing an open annular gap space surrounding the inner tube.

The extension tube assembly can further include a coupling tube extending a distance into the inner lumen of the outer support tube at the first end portion of the outer support tube and extending a distance out of the inner lumen and into the first connector. The inner coupling tube can be closely spaced apart from and can surround the inner tube and has a length that is in a range of about 0.1 inches and about 1 inch. The assembly can also include an adapter sleeve coupled to an outer surface of the support tube and an outer surface of the first connector.

The second connector can have an outer wall surrounding an inner channel. The inner channel can have a first segment that holds the second end portion of the outer support tube. The second connector can have a projecting member that is axially aligned with and has an end that extends forward of the outer support tube and out of the primary body of the second connector. The second connector can have an open cavity between the outer wall and the projecting member. The projecting member can have a tapered axially extending channel. The inner tube can extend through the tapered axially extending channel and terminates at the end of the projecting member.

Still other embodiments are directed to methods of transferring a substance to and/or from a patient. The methods include: providing an extension tube assembly with a flexible outer tube surrounding an inner tube and longitudinally opposing first and second connectors; providing a cannula assembly with a flexible outer tube surrounding an axially extending inner tube and a tubular cannula having an axially extending interior lumen holding the or an axially extending fused silica glass inner tube with a length sufficient to define a tip of a needle that resides outside a distal end of the tubular cannula; coupling the extension tube assembly to the cannula assembly with the inner tubes thereof axially aligned and in fluid communication; coupling the first connector to a dispensing end of a syringe; and inserting the distal end of the tubular cannula and inner tube defining the tip of the needle into a patient; then transferring a substance to or from a target site through a lumen at the tip of the needle.

Optionally the methods can include coupling a filter in-line with and between the extension tube assembly and the cannula assembly before the inserting and/or transferring steps.

Further optionally, the transferring the substance to or from the target site can be carried out by infusing a substance.

Further optionally, the inner tubes can be PEEK or fused silica glass.

Embodiments of the invention are directed to intrabody fluid transfer assemblies with a tubular cannula having a fixed or adjustable cannula to needle tip length that are coupled to the extension tube assembly, related systems and methods.

Embodiments of the invention are directed to an infusion system with an infusion cannula that is coupled to an extension tube that resides between a syringe and the infusion cannula.

Embodiments of the invention are directed to infusion cannula for infusing a medical treatment to an intrabrain target while coupled to an external extension tube assembly in fluid communication with a container, optionally a syringe, of a medical treatment substance.

The extension tube assembly has opposing proximal and distal ends and an axially extending lumen defined by an inner tube of fused silica glass or PEEK. The inner tube can extend through or into a connector at each of the proximal and distal ends. The inner tube resides in (is surrounded by) flexible tubing.

The extension tube assembly can be MM compatible for use in an MRI guided procedure.

The intrabody fluid transfer assemblies can be particularly suitable for withdrawing/introducing fluid from/into the ventricular brain.

The inner tube can have an inner diameter of between about 100 µm and about 750 µm, such as about 200 µm or about 0.200 mm.

Yet other embodiments are directed to methods of transferring a substance to and/or from a patient, the methods include: providing an extension tube assembly with an outer support sleeve surrounding an axially extending inner tube;

providing a tubular cannula coupled to a length of flexible tubing, the flexible tubing and the tubular cannula have an axially extending inner tube defining an interior lumen of small inner diameter (optionally in a range of about 100 μm and about 750 μm, such as about 200 μm or about 0.200 mm) that is in fluid communication with the inner tube of the extension tube assembly; then transferring the substance to or from the target site through the inner tubes.

The transferring the substance to or from the target site can be carried out by infusing a substance into target tissue such as into the brain or into the heart, for example.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 5 is a top view of an example extension tube according to embodiments of the present invention.

FIG. 6 is a section view taken along line 6-6 in FIG. 5.

DETAILED DESCRIPTION

Figure 1:
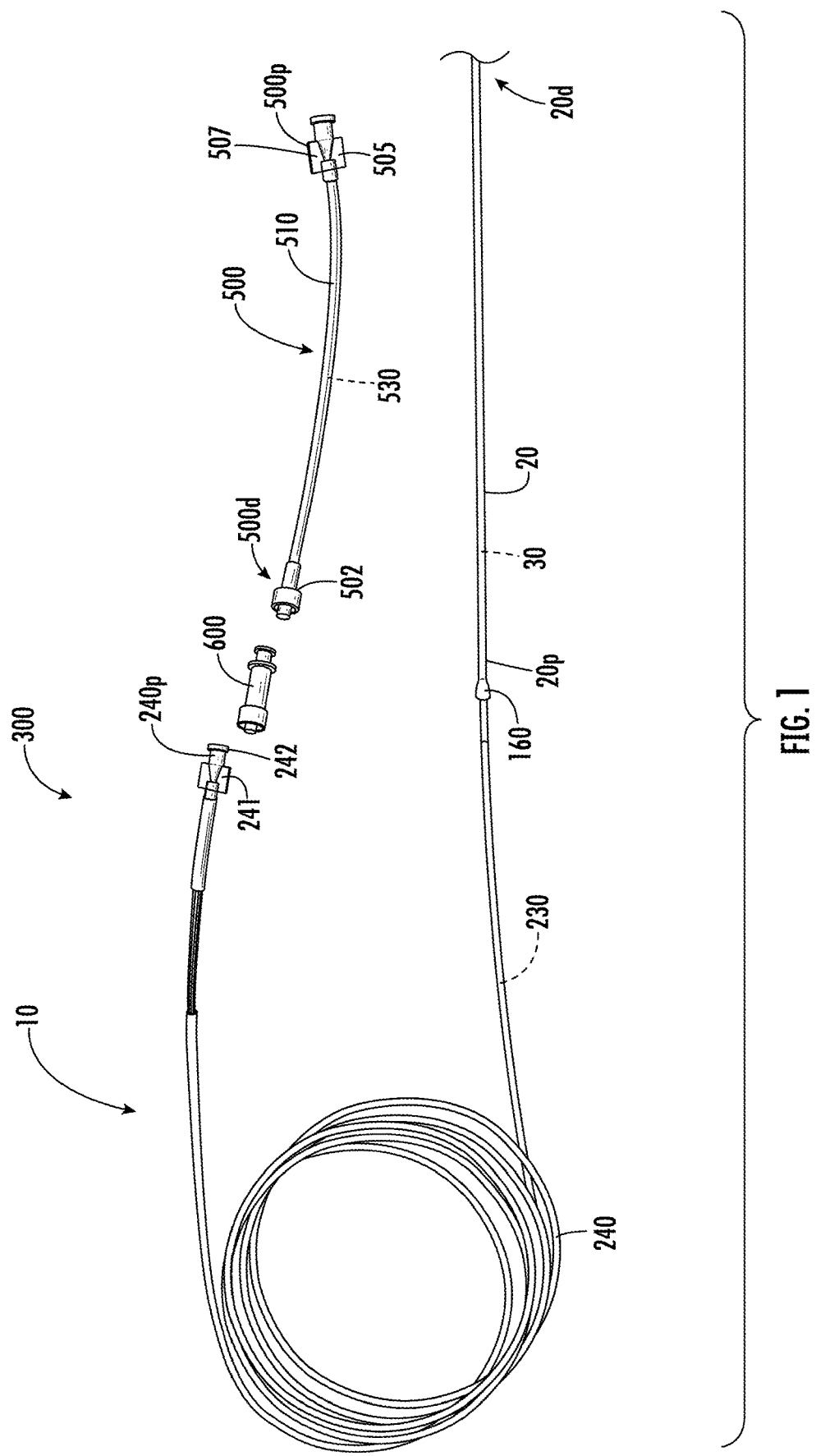
FIG. 1 is a top perspective view of cooperating components of a medical intrabody fluid transfer system, including a cannula assembly and an extension tube according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The terms "FIG." and "Fig." are used interchangeably with the word "Figure" in the specification and/or figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/−twenty percent (20%).

The term "monolithic" means that the component (e.g., inner tube or needle) is formed of a single uniform material.

The term "MRI visible" means that a device is visible, directly or indirectly, in an MRI image. The visibility may be indicated by the increased SNR of the MM signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MM environment and/or can operate as intended in an MRI environment without generating MR signal artifacts and, as such, if residing within the high-field strength region of the magnetic field, is typically made of a non-ferromagnetic MM compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near "real-time" imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The term "sterile," as used herein, means that a device, kit, and/or packaging meets or exceeds U.S./Federal Drug Administration and/or other regulatory medical/surgical cleanliness guidelines, and typically is free from live bacteria or other microorganisms.

Embodiments of the present invention can be utilized with various diagnostic or interventional devices and/or therapies to any desired internal region of an object using any suitable imaging modality, typically an MRI and/or in an MRI scanner or MM interventional suite. However, CT or other imaging modalities may be used. The object can be any object, and may be particularly suitable for animal and/or human subjects for e.g., animal studies and/or veterinarian or human treatments. Some embodiments deliver therapies to the spine. Some embodiments deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat tumors.

The term "substance," as used herein, refers to a liquid for treating or facilitating diagnosis of a condition and can include bions, stem cells or other target cells to site-specific regions in the body, such as neurological, nerves or other target sites and the like. In some embodiments, stem cells and/or other rebuilding cells or products can be delivered into spine, brain or cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The term "fluid" with respect to fluid being withdrawn from a subject refers to soft tissue, foreign matter, biological matter including cellular material and liquid in a subject.

The term "infusion" and derivatives thereof refers to the delivery of a substance (which can be a single substance or a mixture) at a relatively slow rate so that the substance can infuse about a target region. Thus, the term "infusate" refers to a substance so delivered.

The term "semi-rigid" refers to devices that have sufficient rigidity to have a self-supporting fixed shape (typically straight tubular or cylindrical shapes) in the absence of applied bending forces but have sufficient flexibility to be able to bend or deflect without breaking in response to forces applied during insertion into or removal from a trajectory guide (see, for example, 1250t, FIG. 4), then return to its original self-supporting shape upon removal of the applied force(s).

The term "flexible" means that the device(s) does not have sufficient rigidity to have a fixed shape without support and can be rolled, coiled, folded for example.

The subject can be any subject, and may be particularly suitable for animal and/or human subjects for e.g., animal studies and/or veterinarian or human treatments.

Some embodiments aspirate fluid from a target intrabody region such as, for example, a brain. For example, aspiration of fluid from a target structure can debulk it. Debulking the structure can relieve pressure on the surrounding areas. This can be desirable as it can be performed in a less invasive manner than surgical resection. See, U.S. patent application Ser. No. 16/217,222, the contents of which are hereby incorporated by reference as if recited in full herein.

Embodiments of the invention can deliver therapies to the spine.

Embodiments of the invention can deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat a patient with one or more tumors.

Embodiments of the present invention will now be described in further detail below with reference to the figures. FIG. 1 illustrates an exemplary intrabody fluid transfer assembly 10 with a cannula assembly 300. The cannula assembly 300 is coupled to an extension tube assembly 500 comprising an external support tube 510 and a longitudinally extending inner tube 530 of increased rigidity and a different material. The external support tube 510 can be polymeric flexible tubing. The cannula assembly 300 comprises a length of flexible tubing 240 with longitudinally opposing proximal and distal end portions 240p, 240d, respectively. The distal end portion 240d is coupled to a tubular cannula 20 that has increased rigidity relative to the flexible tubing 240. An inner tube 230 extends through the flexible tubing 240 and an inner tube 30 also extends through the tubular cannula 20. The proximal end portion 240p of the flexible tubing 240 can comprise an external tab 241 and a connector 242, such as a luer connector.

Optionally, an in-line filter 600 can extend between the proximal end portion 240p of the flexible tubing 240 and the distal end portion 500d of the extension tube assembly 500. The filter 600 can sealably couple to connectors 242, 502.

The inner tube 30 can extend outside the proximal end 20p and the distal end 20d of the tubular cannula 20.

The extension tube assembly 500 can have opposing proximal and distal end portions 500p, 500d, respectively. As will be discussed further below, the extension tube assembly 500 can have a longitudinally extending inner tube 530 and a connector 502 on the distal end portion 500d and a connector 505 on the proximal end portion 500p. The extension tube assembly 500 can have at least one external tab 507, shown as adjacent the proximal end portion 500p.

The inner tube 230 can be aligned with and couple to the inner tube 30 in the tubular cannula 20 and to the inner tube 530 in the extension tube assembly 500.

The inner tube 230 in the flexible tubing 240 can be provided as a separate tube from the inner tube 30 that extends through the tubular cannula 20. If provided as separate tubes 30, 230, the tubes 30, 230 can have the same inner diameter, on average, and can be fluidly connected.

The inner tube 30 of the tubular cannula 20 and the inner tube 230 in the flexible tubing 240 can be a single unitary tube of continuous length and may have a constant inner diameter, at least over a major portion of a length thereof.

In some embodiments, the inner tube 230 in the flexible tubing 240 can be one continuous piece of material, typically of either PEEK or fused silica glass, that goes from the distal end portion 240d of the tubing 240 to a connector 160 at the proximal end portion 240p. The connector 160 can couple to connector 60 on the proximal end of the cannula 20. Typically the inner tube 230 and the flexible tubing 240 have a length that is between about 4 feet to about 10 feet long.

The extension tube assembly 500 can have a length "L" that is less than that that of the flexible tubing 240, typically 50% to 90% less than the length of the flexible tubing 240. The extension tube assembly 500 can have a length L that is about 2 feet to about 2 inches, including about 2 feet, about 1.5 feet, about 1 foot, about 11 inches, about 10 inches, about 9 inches, about 8 inches, about 7 inches, about 6 inches, about 5 inches, about 4 inches, about 3 inches and about 2 inches.

The extension tube assembly 500 can couple to the tubing 240 with the inner tube 230 which can couple to the inner tube 30 in the tubular cannula 20. The extension tube assembly 500 can reside closer to and couple directly to the pump P (FIG. 3) or other pressurized source for delivery or vacuum.

Referring to FIG. 1, the inner tubes 30, 230, 530 can be inner tubes of a small inner diameter defining a liquid flow channel. The small inner diameter can be in a range of range of 100 μm to about 750 μm, such as about 200 μm, or in a range of about 0.20 mm to about 0.05 mm, such as about 0.20 mm or about 0.053 mm. The inner tubes 30, 230, 530 can be formed of PEEK or fused silica glass, or combinations thereof. The inner tubes 30, 230, 530 can have the same size inner diameter at least over a major portion of a respective length of each tube 30, 230, 530. Each tube 30, 230, 530 can be axially aligned and coupled to be in fluid communication. The inner tube 530 in the extension tube assembly 500 can reduce dead waste in the lumen when a delivery such as an infusion procedure is complete. The fused silica glass or PEEK or other material forming one or more of the inner tubes 30, 230, 530, can be substantially, if not totally, inert and sterile, so as not to chemically interact with any fluid in the lumen.

The inner tube 30 of the tubular cannula 20 can define an external needle tip 30t. The inner tube 30 can release or intake fluid from a subject at a target intrabody site via an open channel extending through the inner tube 30 via a port at the tip 30t.

The cannula assembly 300 can comprise concentric inner and outer tubes 30, 33 that are coupled to and reside inside the tubular cannula 20. The outer tube 33 can have a lesser length than the inner tube 30.

The inner tube 30 can reside a distance outside the tubular cannula 20 and the outer tube 33 can reside a distance outside the tubular cannula 20 but at a lesser distance than the inner tube 30 and terminate before the tip 30t of the inner tube 30.

The inner tube 30 and the outer tube 33 can have a fixed configuration and length relative to the tubular cannula 20.

Figure 4:
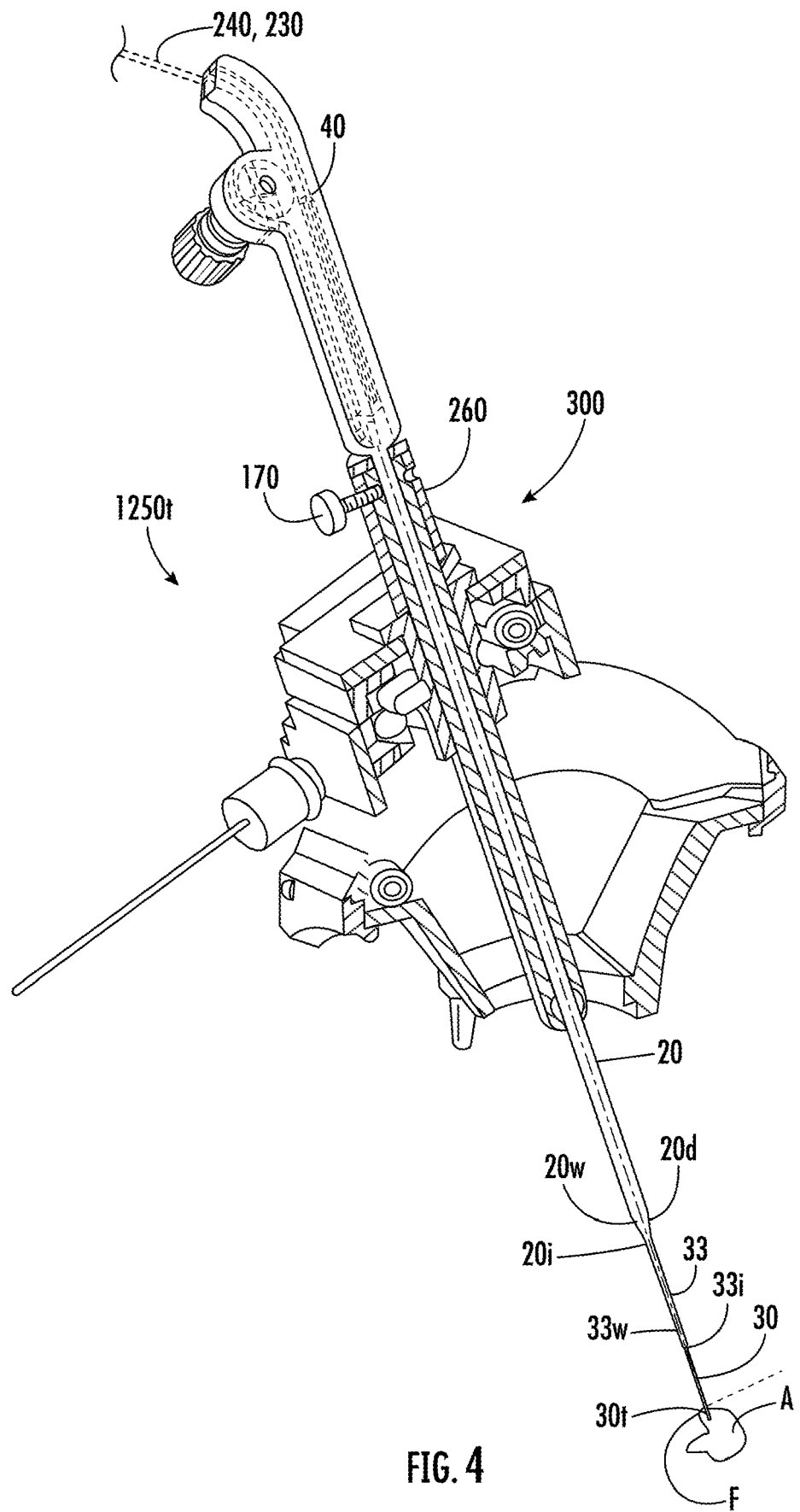
FIG. 4 is an enlarged partial section view of an example cannula of the cannula assembly shown in FIGS. 1 and 2, held by a trajectory guide for intrabody placement of a needle tip of the cannula assembly, according to embodiments of the present invention.

Referring to FIG. 4, the outer tube 33 can be closely spaced to the inner surface 20i of the outer wall 20w of the tubular cannula 20 and the inner tube 30 can be closely space to the inner surface 30i of the wall 33w of the outer tube 33 to inhibit reverse flow and/or provide a fluid-resistant interface to inhibit flow therebetween. The outer tube 33 can be affixed to the inner tube 30 and can have an interference fit with the tubular cannula 20.

Figure 2:
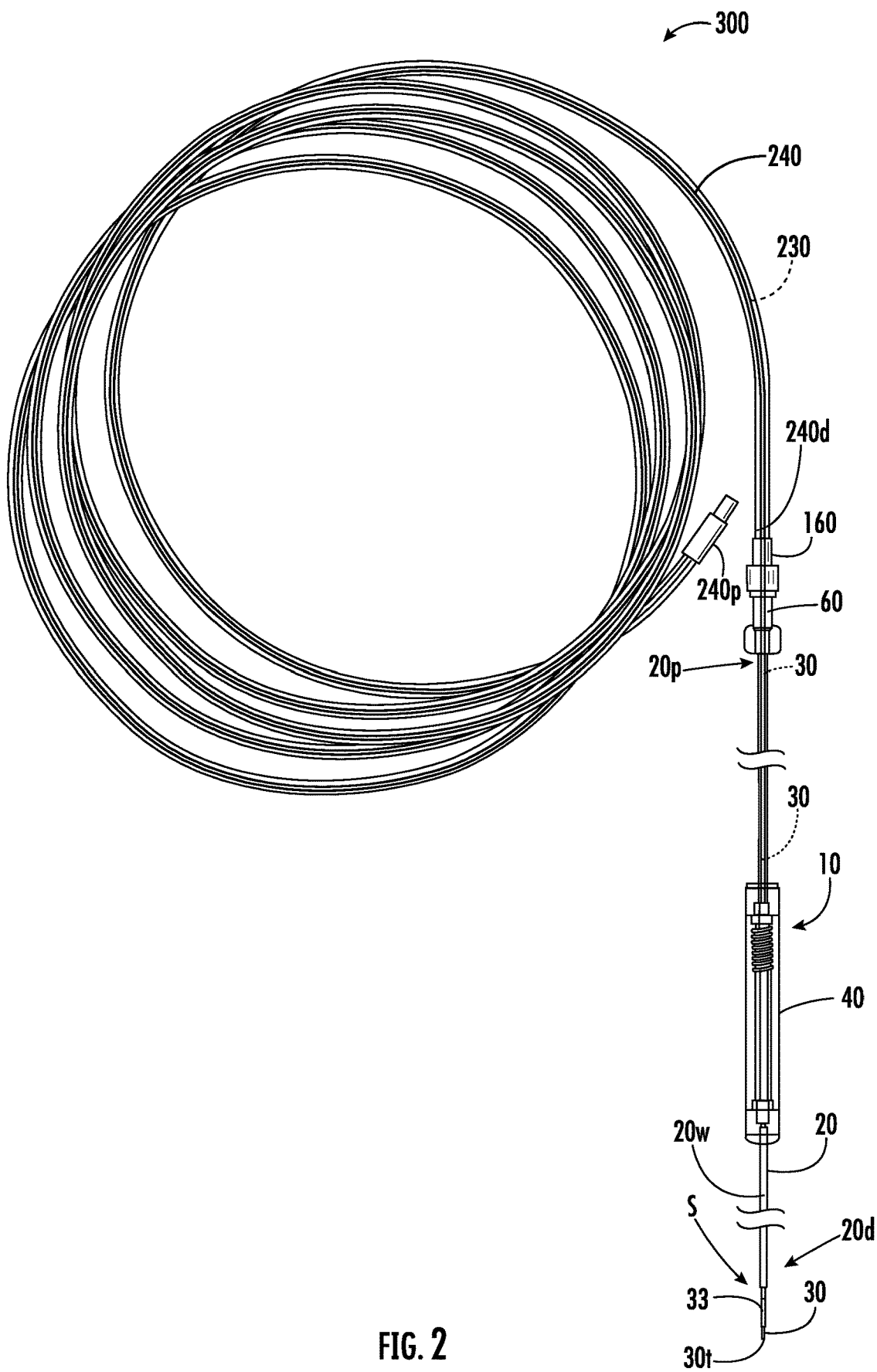
FIG. 2 is a top view of an example cannula assembly for the medical intrabody fluid transfer system shown in FIG. 1 according to embodiments of the present invention.

Optionally, one or all of the tubular cannula 20, inner tube 30 and outer tube 33 can be configured to extend and retract relative to each other and may include a length adjustment mechanism 40 as shown in FIGS. 2 and 4. See, U.S. patent application Ser. No. 15/420,685, the contents of which are hereby incorporated by reference as if recited in full herein. The length adjustment mechanism can be configured to adjust a distance or length between the distal end portion 20d of the tubular cannula 20 and the exposed tip 30t of the needle 30. The length adjustment mechanism can be configured to provide a maximal stroke length of between 0.5 inches and 3 inches, more typically between about 0.75 inches to about 1 inch (2.5 cm) such as about 0.79 inches. The length adjustment can be carried out in vivo while the housing remains external of a patient with the distal end 20d of the cannula 20 and needle tip 30t in the body of the patient.

The tubular cannula 20, the inner tube 30 and the outer tube 33 can define a series of (typically between two-six) steps S of concentric changes (reduction in a direction toward the tip 30t) in outer diameter size between a distal end portion 20d of the tubular cannula 20 and the tip 30t of the inner tube 30 as shown in FIG. 2. The steps S can be configured to inhibit reflux. Each or one or more of the steps can define a surface that is orthogonal to an outer wall 20w of the tubular cannula 20 and/or a longitudinally extending tubular cannula body axis.

The needle tip 30t can reside at a short distance from the distal end of the cannula 20d such as in a range of about 1 mm to about 1.5 inches, typically between 1 mm and 1.1 inches.

The flexible tubing 240 and the external support tube 510 can be MM compatible. The external support tube 510 of the extension tube assembly 500 can be of a different material and/or have a different configuration (wall thickness, etc.) than the flexible tubing 240. According to some embodiments, the flexible tubing 240 and the support tube 510 are both flexible PVC tubing. According to some embodiments, the flexible tubing 240 and the external support tube 510 comprise silicone tubing.

The tubular cannula 20 can have a rigid body. The cannula 20 may comprise alumina/ceramic that can be MM visible. The cannula 20 can have an outer surface having a lubricious coating and/or sleeve 23. The coating and/or sleeve can be a substantially transparent polymeric material. Where a sleeve is used, the sleeve 23 can be a thin flexible polymeric sleeve that can be conformably attached to the underlying cannula body. The coating and/or sleeve can be configured with sufficient strength to be able to retain components of the cannula should the cannula fracture. The sleeve can be an elastomeric shrink wrap or tube that can be heat-shrink applied to the underlying body.

Figure 3:
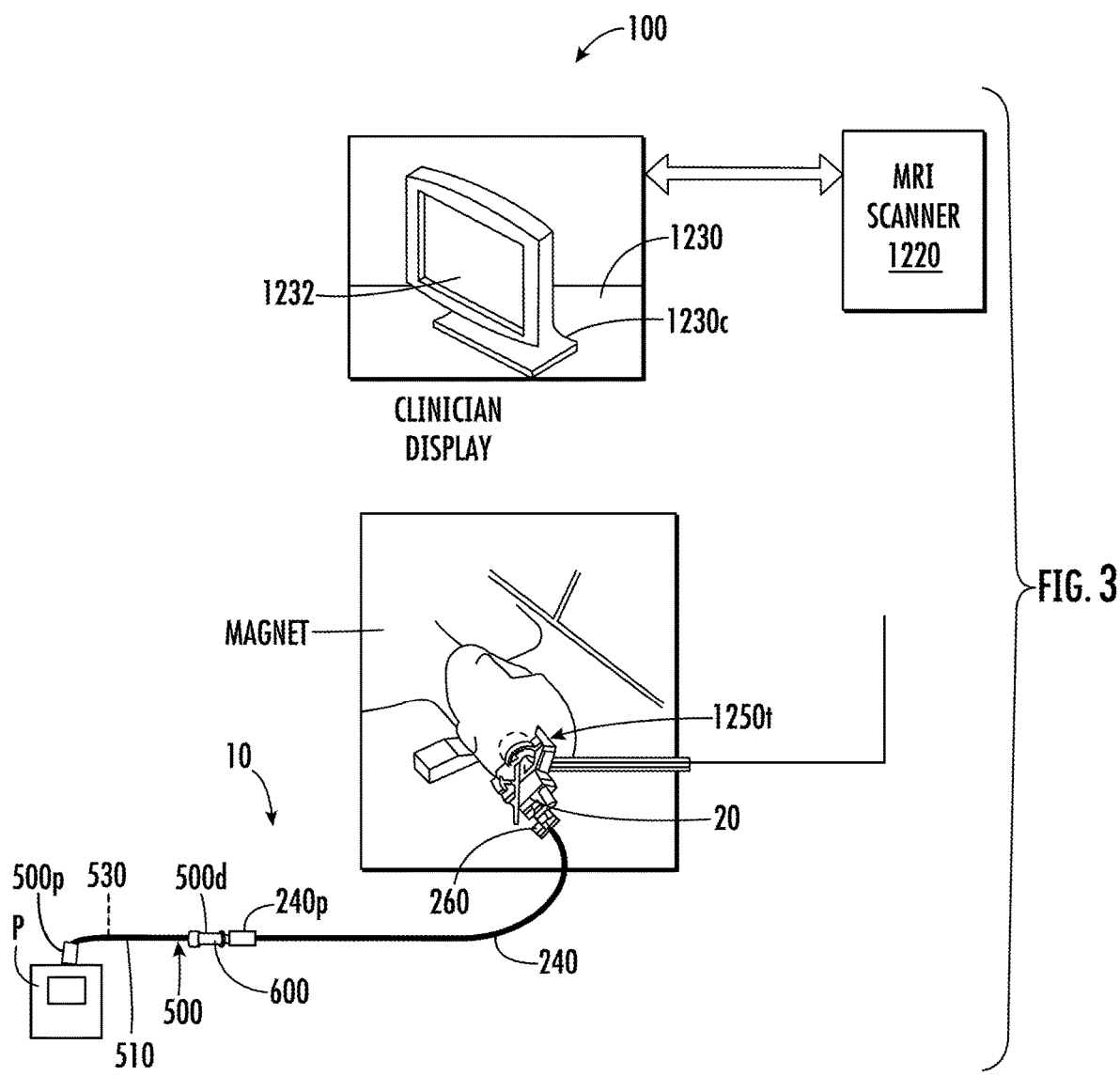
FIG. 3 is a schematic illustration of a medical intrabody fluid transfer system operable in an image guided surgical navigation system according to embodiments of the present invention.

Referring to FIGS. 3 and 4, the tubular cannula 20 can extend through a tubular support 260 of a trajectory guide 1250t that can be held by a base or frame, e.g., a stereotactic frame that can be secured to the patient or that can be secured to a holder residing over the patient. A lock 170 can be used to secure the tubular cannula 20 at a desired position in the tubular support 260 and the tubular cannula 20 with needle tip 30t can extend into a patient to place the needle tip and a target region A and withdraw or delivery substance F. See, e.g., U.S. Pat. Nos. 8,315,689, 8,175,677 and 8,374,677 and US Patent Application Publication No. 2010/0198052 (Ser. No. 12/694,865) for descriptions of patient planning and entry protocols and frames and trajectory guides, the contents of which are hereby incorporated by reference as if recited in full herein.

FIG. 3 illustrates an MM-guided interventional system 100 with an MRI scanner 1220, a clinician workstation 1230 with at least one circuit 1230c, at least one display 1232, an MRI compatible trajectory guide 1250t and a fluid transfer assembly 10. In some embodiments, the fluid transfer assembly 10 can cooperate with an infusion pump P which can be manual or automated and may include a syringe, or another pressurized delivery or vacuum source.

The system 100 can be configured to render or generate near real time or real time visualizations of the target anatomical space using MRI image data and predefined data of at least one surgical tool (e.g., tubular cannula 20 and/or trajectory guide 1250t) to segment the image data and place the trajectory guide 1250t and the cannula 20 in the rendered visualization in the correct orientation and position in 3D space (which is the MM surgical space for MRI embodiments), anatomically registered to a patient. The trajectory guide 1250t and the cannula 20 can include or cooperate with tracking, monitoring and/or other interventional components.

An exemplary trajectory guide 1250t is illustrated in FIG. 3 in an exemplary (head) position on a patient. However, the trajectory guide can be used for any target location including, for example, the spine. The trajectory guide 1250t can be mounted over or on an object, e.g., patient or subject, so that the upper receiving tube/support column 260 (FIG. 4 is oriented substantially perpendicular to the entry location (typically for spinal uses) or may be mounted to extend outward from the patient entry location at an angle.

The trajectory guide 1250t can be configured to provide one or more of an X-Y adjustment and/or pitch and roll adjustment in order to accurately position the cannula 20 at a desired location within a patient. For additional discussion of examples of suitable trajectory guides, see U.S. Pat. No. 8,374,677, the contents of which are hereby incorporated by reference as if recited in full herein. However, it is noted that other trajectory guide configurations may be used and embodiments of the invention are not limited by the examples of the trajectory guides herein.

According to some embodiments, the systems are configured to provide a substantially automated or semi-automated and relatively easy-to-use MRI-guided system with defined workflow steps and interactive visualizations. In particular embodiments, the systems define and present workflow with discrete steps for finding target and entry point(s), guiding the alignment of the targeting cannula to a planned trajectory, monitoring the insertion of the tubular cannula 20, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

The system 100 may also include a decoupling/tuning circuit that allows the system to cooperate with an MRI scanner 1220 and filters and the like. See, e.g., U.S. Pat. Nos. 6,701,176; 6,904,307 and U.S. Patent Application Publication No. 2003/0050557, the contents of which are hereby incorporated by reference as if recited in full herein.

Referring now to FIGS. 5-8, example features of the extension tube assembly 500 will be further discussed. The inner tube 530 of the extension tube assembly 500 extends as a continuous tube defining an inner flow lumen through the support tube 510 and at least partially into the opposing distal and proximal connectors 502, 505 coupled to respective opposing distal and proximal end portions 510d, 510p of the external support tube 510.

Figure 7:
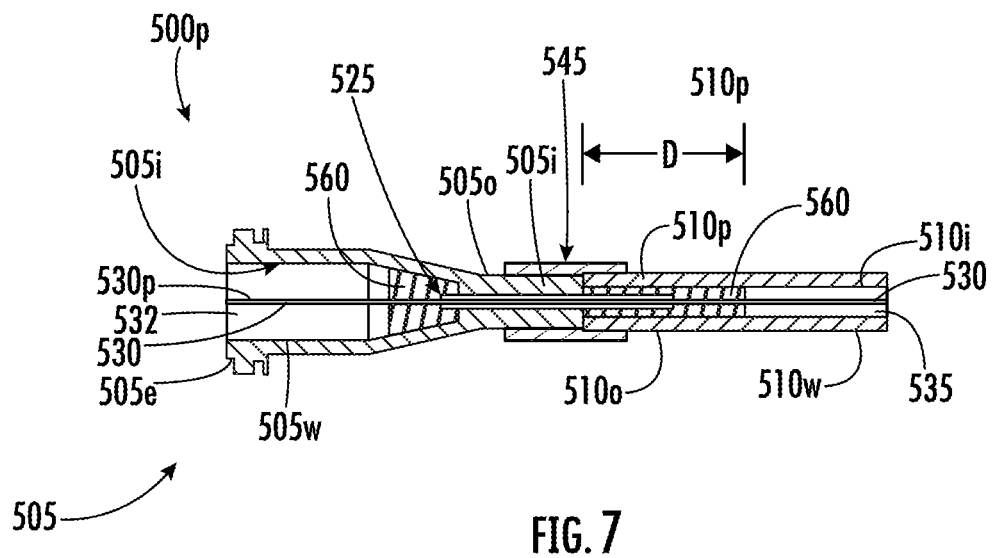
FIG. 7 is an enlarged view of detail B shown in FIG. 6.

As shown in FIG. 7, the proximal end portion 510p of the external support tube 510 terminates adjacent an inner facing end 505i of the connector 505 while the proximal end 530p of the inner tube extends into the connector 505 and terminates adjacent an outer facing end 505e of the connector 505.

A coupling tube 525 can optionally be used at the connector 505 and support tube 510 interface. The coupling tube 525 can be concentric with and surround a small length of the inner tube 530 and can extend into the connector 505 and into the external support tube 510 a distance that is typically about 0.25 inches to about 2 inches to provide additional bonding surface area. The (inner) coupling tube 525 can be in contact with or within about 1 mm from the outer surface of the inner tube 530.

An outer adapter sleeve 545 can extend about an outer surface 510o of the support tube 510 and an outer surface 505o of the connector 505 and couple the proximal end 510p of the support tube 510 and the inner facing end 505i of the connector 505.

A gap space 532 can extend (longitudinally and circumferentially) between the inner tube 530 and an inner surface 505i of an outer wall 505w of the connector 505, surrounding the proximal end 530p of the inner tube 530. The connector 505 can be a female luer lock connector.

An annular gap space 535 can extend (circumferentially and longitudinally) between the inner tube 530 and an inner surface 510i of an outer wall 510w of the support tube 510.

The coupling tube 525 can extend axially a distance into the gap space 532 and gap space 535. A portion of the gap space 535 facing the connector 505 and into which the coupling tube 525 resides can comprise a filler material 560, typically a filler material that can be applied in liquid form and solidified into a solid, such as a semi-rigid or flexible solid, surrounding an outer surface of the inner tube 530. The filler material 560 can comprise epoxy and/or one or more different formulations of LOCTITE adhesive and/or mixtures thereof. Optionally, LOCTITE UV adhesive 3311 and LOCTITE adhesive 4010. An outer facing portion of the gap space 532 in the connector 505 can remain open and surrounded by air. An inner facing portion of the gap space 535 in the support tube 510 can remain open and surrounded by air or gas.

The open inner facing portion of the gap space 535 can extend over at least a major length of the support tube 510, shown in FIG. 6 as an open annular gap space extending continuously between opposing proximal and distal end portions 510p, 510d of the support tube 510.

FIG. 7 illustrates that the filler material 560 resides in the gap space 535 a small distance D, typically a distance D in a range of about 0.24 inches and about 1 inch.

Figure 8:
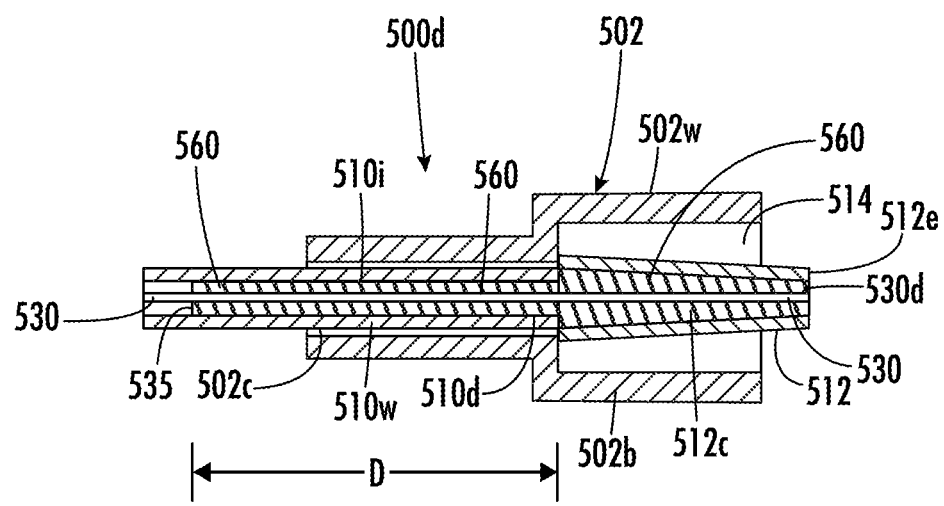
FIG. 8 is an enlarged view of detail C shown in FIG. 6.

FIG. 8 illustrates that the distal end portion 510d of the support tube 510 is coupled to a connector 502. The distal end portion 510d of the support tube 510 can have an annular gap space 535 that can extend (circumferentially and longitudinally) between the inner tube 530 and an inner surface 510i of an outer wall 510w of the support tube 510.

Filler material 560 can reside in the gap space 535 a sub-length of the annular space, such as a small distance D, typically a distance D in a range of about 0.24 inches and about 1 inch.

The filler material 560 can comprise epoxy that bonds components together at the distal and proximal end portions of the support tube 510. The filler material can wick into the annular space 535 up to about an inch at both ends 510p, 510d of the support tube 510. The filler material 560 can create a good bond and also act as a strain relief so that the connector 502 and/or 505 does not kink in that region (stiff connection of respective luer fitting) and inhibits breakage of the inner tube 530.

The connector 502 can have a primary body 502b with an outer wall 502w surrounding an axially projecting member 512 that extends a longitudinal distance beyond the outer wall 502w. The connector 502 has an inner channel 502c which holds a segment of the outer support tube 510. The connector 502 can be a male luer lock connector. The inner tube 530 extends through the projecting member 512 to terminate flush or adjacent an outer facing end 512e of the projecting member 512. Filler material 560 can extend about and surround the inner tube inside the projecting member 512. The filler material 560 can occupy all the space between the inner tube 530 and the internal cavity 512c of the projecting member 512. The connector 502 can have an open gap space 514 surrounding the projecting member 512 between the projecting member 512 and the outer wall 502w.

Figure 9:
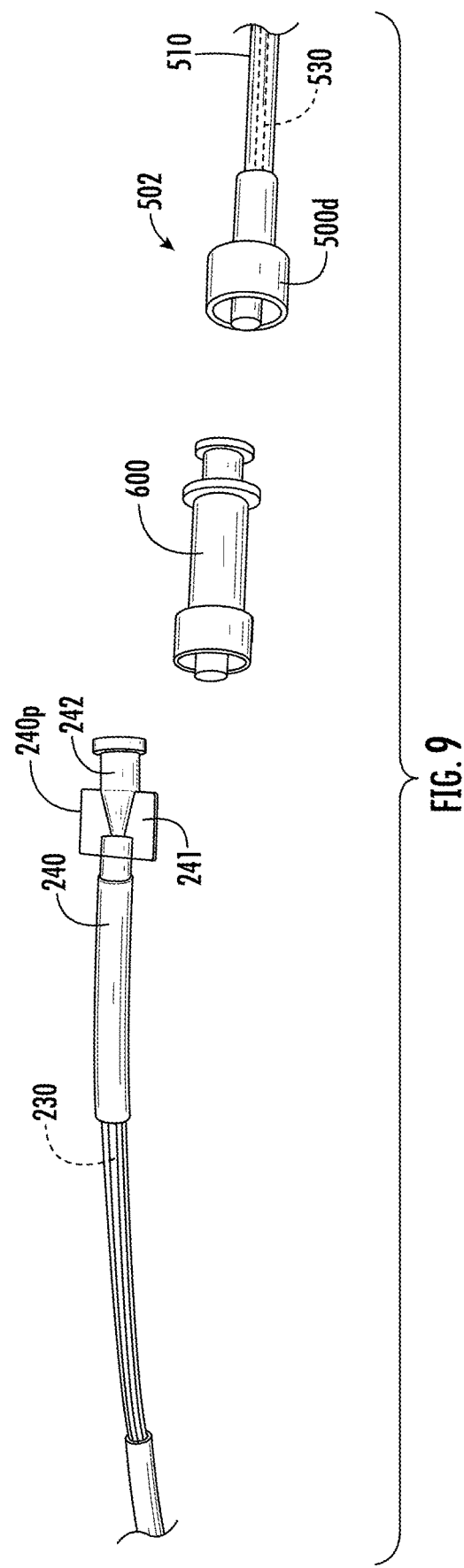
FIG. 9 is a top perspective unassembled view of portions of cooperating components of the intrabody fluid transfer system according to embodiments of the present invention.
Figure 10:
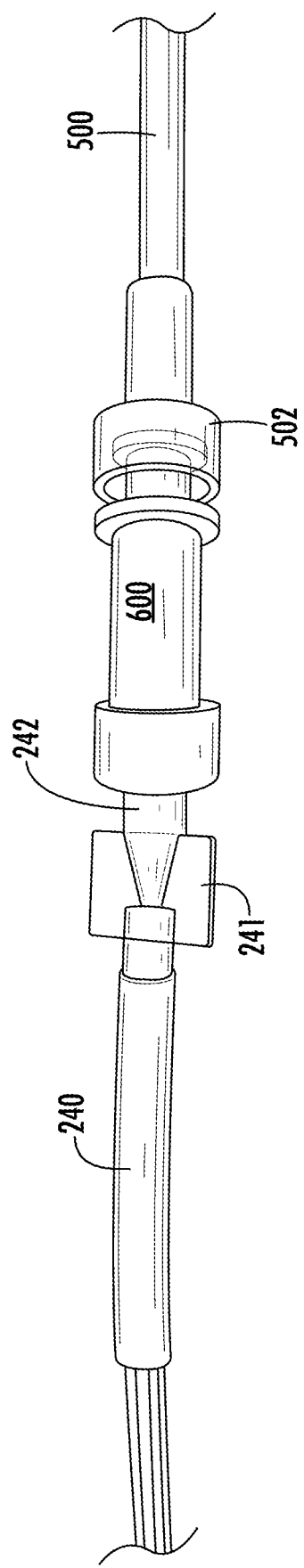
FIG. 10 is a top assembled view of the components shown in FIG. 9.

FIG. 9 illustrates a proximal end 240p of the flexible tubing 240 with the connector 242 aligned with an optional filter 600 and with the connector 502 on the distal end portion 500p of the extension tube assembly 500. FIG. 10 illustrates these components sealably coupled together placing the tubes 530, 230 and 30 in fluid communication.

Figure 11:
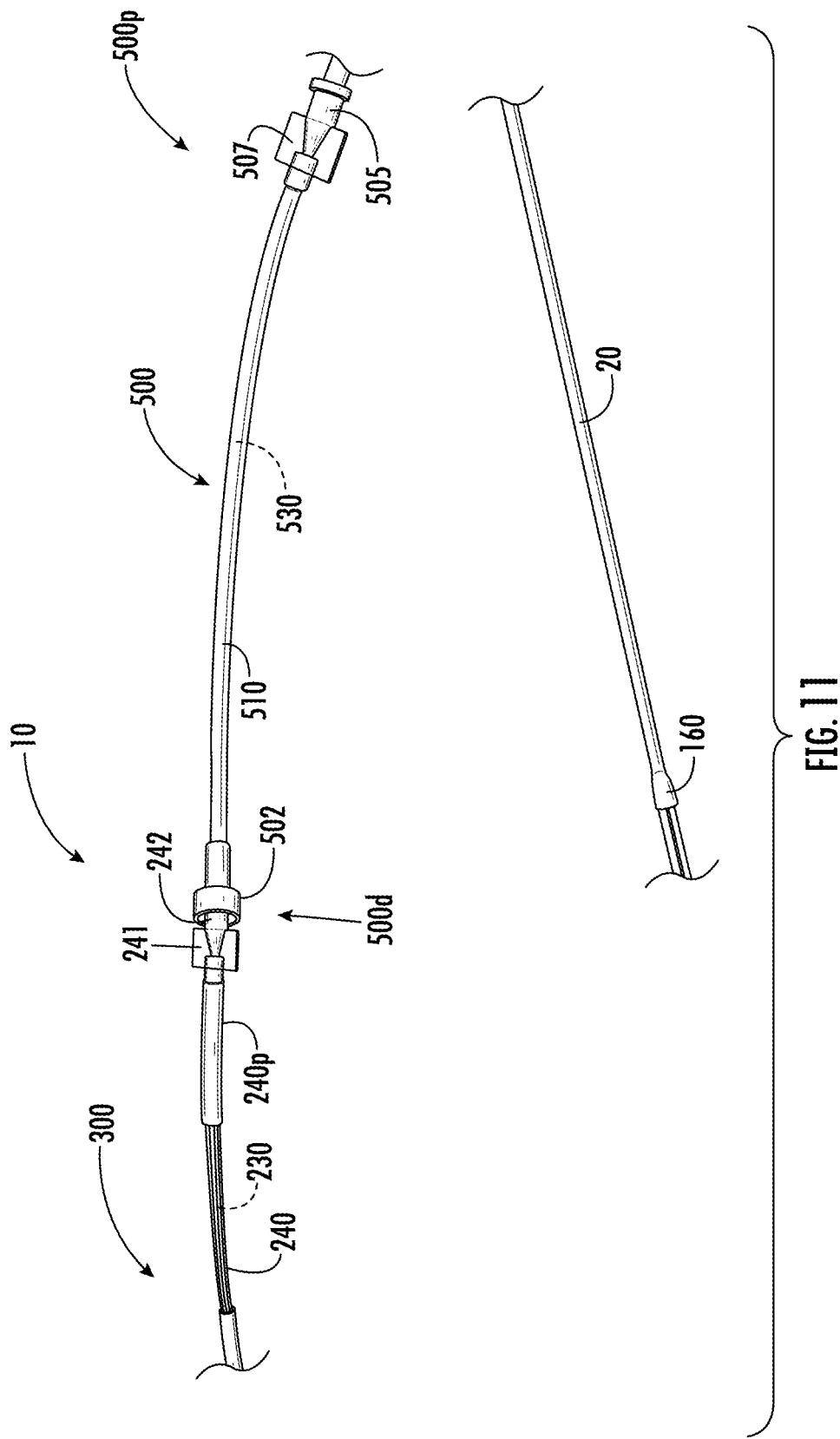
FIG. 11 is a top perspective assembled view of the assembly shown in FIG. 10 illustrating the flexible tubing and cannula of the intrabody fluid transfer system and a portion of the flexible tubing coupled to the cannula according to embodiments of the present invention.

FIG. 11 illustrates the intrabody fluid transfer assembly 10 assembled without the use of the filter 600.

Figure 12:
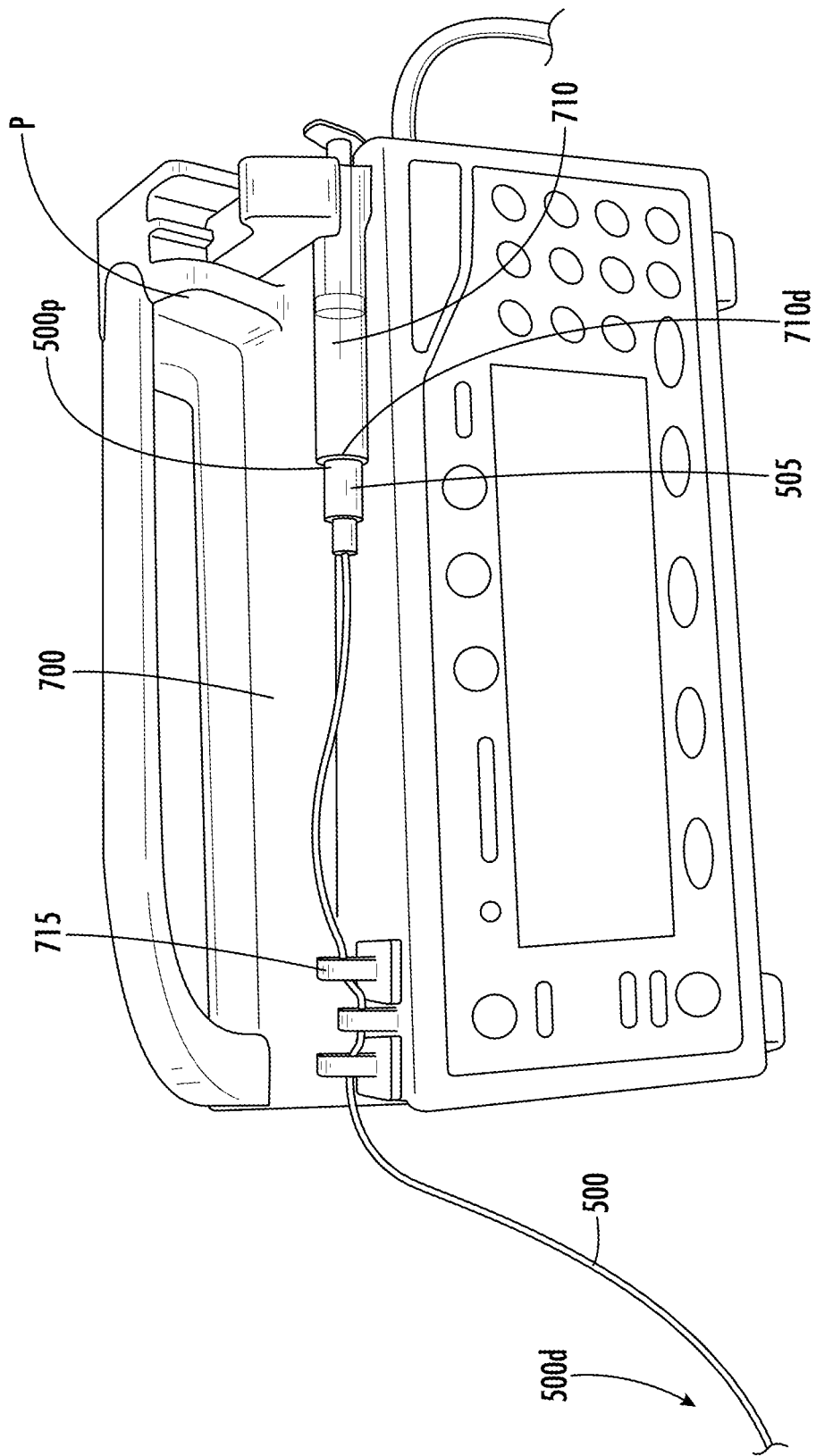
FIG. 12 is a side perspective, partial view of the extension tube held by a syringe pump body and coupled to a syringe for fluid transfer according to embodiments of the present invention.

FIG. 12 illustrates the extension tube assembly 500 held by a housing 700 of a pump P placing the proximal end portion of the extension tube assembly adjacent a syringe 710. The connector 505 can directly engage a dispensing port 710d of the syringe 710 thereby placing inner tube 530 against a tip of the syringe dispensing port 710d. The housing 700 can include attachment members 715 that slidably and detachable receive a segment of the extension tube assembly 500.

The assembly 10 can be configured to flowably introduce, infuse and/or inject a desired therapy substance (e.g., antigen, gene therapy, chemotherapy or stem-cell or other therapy type).

In some embodiments, the intrabody fluid transfer assembly 10 is configured to deliver a drug therapy to the brain. The drug therapy can comprise substance F (FIG. 4 15) delivered to the target site or region A through the inner tube 30 and may be any suitable and desired substance for drug discovery, animal or human clinical trials and/or approved medical procedures. According to some embodiments, the substance F is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dendritic cells). The dendritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance F may comprise radioactive material such as radioactive seeds. Substances F delivered to a target area in accordance with embodiments of the present invention may include, but are not limited to, the following drugs (including any combinations thereof) listed in Table 1:

TABLE 1

| DRUG (generic name) | DISORDER(S) |
| --- | --- |
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |

TABLE 1-continued

| DRUG (generic name) | DISORDER(S) |
|---|---|
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |

TABLE 1-continued

| DRUG (generic name) | DISORDER(S) |
|---|---|
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| 1-methylfolate | Depression & BPD |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |

TABLE 1-continued

| DRUG (generic name) | DISORDER(S) |
|---|---|
| Thioridazine | Schizophrenia & Psychosis |
| Cytarabine | Chemotherapy, hematological malignancies |

According to some embodiments, the intrabody fluid transfer system 10 can be configured as an infusate delivery system that is delivered to a patient at an infusion rate in the range of from about 1 to about 3 μL/minute.

Insertion of the surgical tubular cannula 20 (or any other surgical, e.g., delivery, cannula) can be tracked in near real time by reference to a void in the patient tissue caused by the cannula 20 and reflected in the MR image. In some embodiments, one or more MRI-visible fiducial markers may be provided on the surgical tubular cannula 20, MR scanned and processed, and displayed on the UI. In some embodiments, the surgical cannula 20 may itself be formed of an MM-visible material, MR scanned and processed, and displayed on the UI.

According to some embodiments, the surgical cannula 20 may include an embedded intrabody MRI antenna (not shown) that is configured to pick-up MRI signals in local tissue during an MRI procedure. The MM antenna can be configured to reside on a distal end portion of the surgical cannula. In some embodiments, the antenna has a focal length or signal-receiving length of between about 1 cm to about 5 cm, and typically is configured to have a viewing length to receive MRI signals from local tissue of between about 1-2.5 cm. The MRI antenna can be formed as comprising a coaxial and/or triaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. 2003/0050557; 2004/0046557; and 2003/0028095, the contents of which are also hereby incorporated by reference as if recited in full herein.

While the intrabody fluid transfer system 10 with the extension tube assembly 500 and the cannula assembly 300 with the surgical cannula 20 and inner tube 30 have been described by way of example as delivery devices and methods for delivering a substance to a patient, in accordance with some embodiments of the invention, the devices can be used to withdraw and/or aspirate a substance (e.g., spinal fluid, cardiac fluid or neuro fluid) from a patient. Thus, it will be appreciated that the devices and methods as disclosed herein can be used to transfer a substance into and/or from a patient.

While the devices have been described herein primarily with reference to MRI-guided insertion and infusion procedures, in some embodiments the devices can be used in procedures without MRI guidance, such as using other imaging modalities where image-guided surgical navigation is desired.

While the intrabody fluid transfer system 10 has been described with the surgical tubular cannula 20 coupled to a trajectory guide 1250*t*, the cannula 20 may be used with other types of trajectory guidance or stereotactic frames or without a stereotactic frame or trajectory guide.

Also, while the extension tube assembly 500 has been described for use with the cannula assembly 300 having the flexible tubing 240 with the inner tube 230, it is contemplated that the extension tube assembly 500 can have sufficient length to directly couple to the connector 60 (FIG. 2) at the distal end portion of the cannula 20 without requiring the intermediate flexible tubing 240 and inner tube 230.

Figure 13:
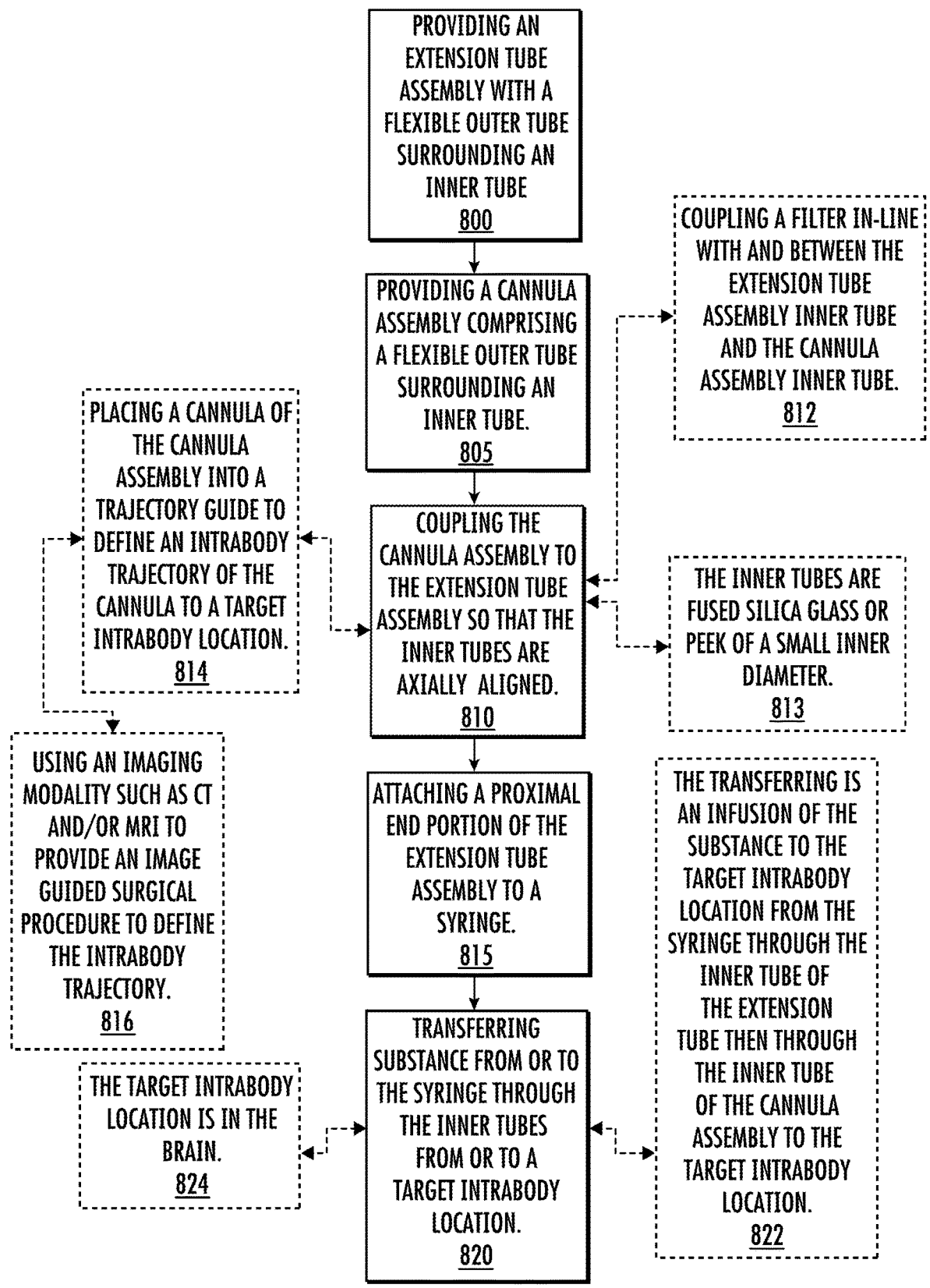
FIG. 13 is a flow chart of exemplary actions that can be carried out according to embodiments of the present invention.

FIG. 13 is a flow chart of exemplary actions that can be carried out according to embodiments of the present invention. An extension tube assembly with a flexible outer tube surrounding an inner tube is provided (block 800). A cannula assembly comprising a flexible outer tube surrounding an inner tube is also provided (block 805). The cannula assembly is coupled to the extension tube assembly so that the inner tubes of each are axially aligned (block 810). A proximal end portion of the extension tube assembly is coupled to a syringe (block 815), typically via a luer connector on the extension tube assembly coupled directly to a dispensing end of the syringe. Substance is transferred from or to the syringe, through the inner tubes from or to a target intrabody location (block 820).

Optionally coupling a filter in-line with and between the inner tube of the extension tube assembly and the inner tube of the cannula assembly (block 812).

The inner tubes are of a small inner diameter, optionally fused silica glass or PEEK inner tubes (block 813).

A rigid or semi-rigid cannula of the cannula assembly can be placed into a trajectory guide to define an intrabody trajectory of the cannula to a target intrabody location (block 814).

An imaging modality can be used, such as CT and/or MRI, to provide an image guided surgical procedure to define the intrabody trajectory (block 816).

The target intrabody location can be the brain (block 824).

The inner tube of the cannula assembly can define an external needle tip and can be fixedly attached to an outer tube that defines an increased diameter outer wall segment a distance of about 1-5 mm, typically about 3 mm from the tip.

The extension tube assembly and cannula assembly can be an infusate ventricular delivery system for brain delivery of a target substance to a target anatomical region. For example, the device can be configured to allow a single intrabody insertion of the cannula/inner tube thereof, to a target anatomical region in the brain (such as tissue generally in-line with and between the nose and back of the head and, starting dispensing/infusing from the back of the head while translating the distal end of the cannula/inner tube thereof frontward to treat a large volume through one intrabody insertion of the cannula/inner tube thereof.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this That which is claimed is:

1. A medical extension tube assembly for transferring fluid to or from a subject, comprising:
an outer support tube having an inner lumen and a length and opposing first and second end portions;
an inner tube longitudinally extending inside the inner lumen of the outer support tube and defining a longitudinally extending open fluid flow path;
a first connector coupled to the first end portion of the outer support tube; and
a second connector coupled to the second end portion of the outer support tube,
wherein the inner tube has an inner diameter in a range of about 100 μm and about 750 μm or in a range of about 50 μm to about 200 μm,
wherein the inner tube extends out of the first end portion of the outer support tube into the first connector, and wherein the inner tube extends out of the second end portion of the outer support tube into the second connector,
wherein the second connector comprises a projecting member that extends out of a primary body of the second connector, wherein the projecting member has a tapered axially extending channel and an end, and wherein the inner tube extends through the tapered axially extending channel and terminates at the end of the projecting member.

2. The medical extension tube assembly of claim 1, wherein the first connector and the second connector are both luer connectors.

3. The medical extension tube assembly of claim 2, wherein the first connector is a female luer connector and the second connector is a male luer connector.

4. The medical extension tube assembly of claim 1, wherein the inner tube is formed of fused silica glass and/or polyether ether ketone (PEEK).

5. A medical extension tube assembly for transferring fluid to or from a subject, comprising:
an outer support tube having an inner lumen and a length and opposing first and second end portions;
an inner tube longitudinally extending inside the inner lumen of the outer support tube and defining a longitudinally extending open fluid flow path;
a first connector coupled to the first end portion of the outer support tube;
a second connector coupled to the second end portion of the outer support tube, wherein the inner tube has an inner diameter in a range of about 100 μm and about 750 μm or in a range of about 50 μm to about 200 μm,
wherein the inner tube extends out of the first end portion of the outer support tube into the first connector, and wherein the inner tube extends out of the second end portion of the outer support tube into the second connector; and
a solid filler material residing in the inner lumen of the outer support tube and surrounding the inner tube at the first and second end portions, wherein the solid filler material comprises a continuous or discontinuous length with a portion that resides in the first connector and a portion that resides in the second connector.

6. The medical extension tube assembly of claim 5, wherein the inner lumen of the outer support tube defines an open gap space surrounding the inner tube along a sub-length of the length of the outer support tube between the opposing first and second end portions.

7. The medical extension tube assembly of claim 5, wherein the filler material terminates a distance in a range of about 0.25 inches and about 1 inch from an end of the first end portion of the outer support tube, and wherein the filler material terminates a distance in a range of about 0.25 inches and about 1 inch from and an end of the second end portion of the outer support tube.

8. A medical extension tube assembly for transferring fluid to or from a subject, comprising:
an outer support tube having an inner lumen and a length and opposing first and second end portions;
an inner tube longitudinally extending inside the inner lumen of the outer support tube and defining a longitudinally extending open fluid flow path;
a first connector coupled to the first end portion of the outer support tube;
a second connector coupled to the second end portion of the outer support tube, wherein the inner tube has an inner diameter in a range of about 100 μm and about 750 μm or in a range of about 50 μm to about 200 μm, wherein the inner tube extends out of the first end portion of the outer support tube into the first connector, and wherein the inner tube extends out of the second end portion of the outer support tube into the second connector;
a coupling tube extending a distance into the inner lumen of the outer support tube at the first end portion of the outer support tube and extending a distance out of the inner lumen and into the first connector, wherein the coupling tube is closely spaced apart from and surrounds the inner tube and has a length that is in a range of about 0.1 inches and about 1 inch; and
an adapter sleeve coupled to an outer surface of the outer support tube and an outer surface of the first connector.

9. A medical extension tube assembly for transferring fluid to or from a subject, comprising:
an outer support tube having an inner lumen and a length and opposing first and second end portions;
an inner tube longitudinally extending inside the inner lumen of the outer support tube and defining a longitudinally extending open fluid flow path;
a first connector coupled to the first end portion of the outer support tube; and
a second connector coupled to the second end portion of the outer support tube, wherein the inner tube has an inner diameter in a range of about 100 μm and about 750 μm or in a range of about 50 μm to about 200 μm, wherein the inner tube extends out of the first end portion of the outer support tube into the first connector, and wherein the inner tube extends out of the second end portion of the outer support tube into the second connector,
wherein the second connector has an outer wall surrounding an inner channel, wherein the inner channel has a first segment that holds the second end portion of the outer support tube, wherein the second connector comprises a projecting member that is axially aligned with and has an end that extends forward of the outer support tube and out of a primary body of the second connector, wherein the second connector comprises an open cavity between the outer wall and the projecting member, wherein the projecting member has a tapered axially extending channel, and wherein the inner tube extends through the tapered axially extending channel and terminates at the end of the projecting member.

10. The medical extension tube assembly of claim 9, further comprising filler material in the tapered axially extending channel surrounding the inner tube and in the inner lumen of the second end portion of the outer support tube surrounding the inner tube.

11. A medical intrabody fluid transfer system, comprising:
an extension tube assembly comprising:
  an outer support tube having an inner lumen and a length and opposing first and second end portions;
  an inner tube longitudinally extending inside the inner lumen of the outer support tube and defining a longitudinally extending open fluid flow path;
  a first connector coupled to the first end portion of the outer support tube; and
  a second connector coupled to the second end portion of the outer support tube, wherein the inner tube extends out of the first end portion of the outer support tube into the first connector, and
  wherein the inner tube extends out of the second end portion of the outer support tube into the second connector,
a cannula assembly coupled to the extension tube assembly and that resides distal of the extension tube assembly, the cannula assembly comprising:
  a tubular cannula having opposing proximal and distal ends with an open axially extending lumen;
  an elongate inner tube extending through the lumen of the tubular cannula with a distal end defining an exposed needle tip; and
  flexible tubing coupled to the proximal end of the tubular cannula and comprising an inner tube aligned with and in fluid communication with the inner tube extending through the tubular cannula and the inner tube of the extension tube assembly; and
  a filter in-line with and coupled to a distal end portion of the extension tube assembly and a proximal end portion of the flexible tubing, wherein the filter comprises a distal end portion that extends into a proximal connector of the cannula assembly and a proximal end portion that extends into the second connector of the extension tube assembly.

12. A medical intrabody fluid transfer system, comprising:
an extension tube assembly comprising:
  an outer support tube having an inner lumen and a length and opposing first and second end portions;
  an inner tube longitudinally extending inside the inner lumen of the outer support tube and defining a longitudinally extending open fluid flow path;
  a first connector coupled to the first end portion of the outer support tube; and
  a second connector coupled to the second end portion of the outer support tube,
  wherein the inner tube extends out of the first end portion of the outer support tube into the first connector, and wherein the inner tube extends out of the second end portion of the outer support tube into the second connector; and
a cannula assembly coupled to the extension tube assembly and that resides distal of the extension tube assembly, the cannula assembly comprising:
  a tubular cannula having opposing proximal and distal ends with an open axially extending lumen;
  an elongate inner tube extending through the lumen of the tubular cannula with a distal end defining an exposed needle tip; and
  flexible tubing coupled to the proximal end of the tubular cannula and comprising an inner tube aligned with and in fluid communication with the inner tube extending through the tubular cannula and the inner tube of the extension tube assembly,
  wherein the inner lumen of the outer support tube defines an open gap space surrounding the inner tube of the extension tube assembly along a sub-length of the length of the outer support tube between the opposing first and second end portions, wherein the extension tube assembly further comprises a solid filler material residing in the inner lumen of the outer support tube, surrounding the inner tube of the extension tube assembly at the first and second end portions, wherein the filler material is provided as a continuous length or provided as discontinuous segments, wherein a portion of the filler material resides in the first connector and a portion of the filler material resides in the second connector, wherein the filler material terminates in the inner lumen of the outer support tube a distance in a range of about 0.25 inches and about 1 inch from an end of the first end portion of the outer support tube, and wherein the filler material terminates in the inner lumen of the outer support tube a distance in a range of about 0.25 inches and about 1 inch from and an end of the second end portion of the outer support tube.

13. A medical intrabody fluid transfer system, comprising:
an extension tube assembly comprising:
  an outer support tube having an inner lumen and a length and opposing first and second end portions;
  an inner tube longitudinally extending inside the inner lumen of the outer support tube and defining a longitudinally extending open fluid flow path;
  a first connector coupled to the first end portion of the outer support tube; and
  a second connector coupled to the second end portion of the outer support tube,
  wherein the inner tube has an inner diameter in a range of about 100 pm and about 750 pm or in a range of about 50 pm to about 200 pm, wherein the inner tube extends out of the first end portion of the outer support tube into the first connector, and wherein the inner tube extends out of the second end portion of the outer support tube into the second connector; and
a cannula assembly coupled to the extension tube assembly, the cannula assembly comprising:
  a tubular cannula having opposing proximal and distal ends with an open axially extending lumen;
  an elongate inner tube extending through the lumen of the tubular cannula with a distal end defining an exposed needle tip; and
flexible tubing coupled to the proximal end of the tubular cannula and comprising an inner tube aligned with and in fluid communication with the inner tube extending through the tubular cannula and the inner tube of the extension tube assembly,
wherein the extension tube assembly further comprises a coupling tube extending a distance into the inner lumen of the outer support tube at the first end portion of the outer support tube and extending a distance out of the inner lumen and into the first connector, wherein the coupling tube is closely spaced apart from and surrounds the inner tube of the extension tube assembly and has a length that is in a range of about 0.1 inches and about 1 inch, and wherein the extension tube assembly further comprises an adapter sleeve coupled to an outer surface of the outer support tube and an outer surface of the first connector.

14. A medical intrabody fluid transfer system, comprising:
an extension tube assembly comprising:
- an outer support tube having an inner lumen and a length and opposing first and second end portions;
- an inner tube longitudinally extending inside the inner lumen of the outer support tube and defining a longitudinally extending open fluid flow path;
- a first connector coupled to the first end portion of the outer support tube; and
- a second connector coupled to the second end portion of the outer support tube,
- wherein the inner tube has an inner diameter in a range of about 100 pm and about 750 pm or in a range of about 50 pm to about 200 pm, wherein the inner tube extends out of the first end portion of the outer support tube into the first connector, and wherein the inner tube extends out of the second end portion of the outer support tube into the second connector; and
- a cannula assembly coupled to the extension tube assembly, the cannula assembly comprising:
- a tubular cannula having opposing proximal and distal ends with an open axially extending lumen;
- an elongate inner tube extending through the lumen of the tubular cannula with a distal end defining an exposed needle tip; and
- flexible tubing coupled to the proximal end of the tubular cannula and comprising an inner tube aligned with and in fluid communication with the inner tube extending through the tubular cannula and the inner tube of the extension tube assembly,
wherein the second connector has an outer wall surrounding an inner channel, wherein the inner channel has a first segment that holds the second end portion of the outer support tube, wherein the second connector comprises a projecting member that is axially aligned with and has an end that extends forward of the outer support tube and out of a primary body of the second connector, wherein the second connector comprises an open cavity between the outer wall and the projecting member, wherein the projecting member has a tapered axially extending channel, and wherein the inner tube of the extension tube assembly extends through the tapered axially extending channel and terminates at the end of the projecting member.

* * * * *

UNITED STATES PATENT AND TRADEMARK OFFICE
CERTIFICATE OF CORRECTION

| | |
|---|---|
| PATENT NO. | : 11,684,750 B2 |
| APPLICATION NO. | : 16/887161 |
| DATED | : June 27, 2023 |
| INVENTOR(S) | : Peter G. Piferi |

It is certified that error appears in the above-identified patent and that said Letters Patent is hereby corrected as shown below:

In the Specification

Column 4, Line 56: Please correct "MM" to read --MRI--

Column 7, Line 8: Please correct "MM" to read --MRI--

Column 7, Line 15: Please correct "MM" to read --MRI--

Column 7, Line 19: Please correct "MM" to read --MRI--

Column 7, Line 62: Please correct "MM" to read --MRI--

Column 11, Line 6: Please correct "MM" to read --MRI--

Column 11, Line 15: Please correct "MM" to read --MRI--

Column 11, Line 41: Please correct "MM-guided" to read --MRI-guided--

Column 11, Line 56: Please correct "MM" to read --MRI--

Column 15, TABLE 1-continued, Line 21: Please correct "Foscamet" to read --Foscarnet--

Column 19, Line 21: Please correct "MM-visible" to read --MRI-visible--

Column 19, Line 26: Please correct "MM" to read --MRI--

Signed and Sealed this
Twenty-ninth Day of August, 2023

Katherine Kelly Vidal
*Director of the United States Patent and Trademark Office*